United States Patent [19]

Gerster

[11] Patent Number: 4,698,348

[45] Date of Patent: Oct. 6, 1987

[54] 1H-IMIDAZO[4,5-c]QUINOLINES AND THEIR USE AS BRONCHODILATING AGENTS

[75] Inventor: John F. Gerster, Woodbury, Minn.

[73] Assignee: Riker Laboratories, Inc., St. Paul, Minn.

[21] Appl. No.: 798,386

[22] Filed: Nov. 15, 1985

Related U.S. Application Data

[63] Continuation-in-part of Ser. No. 785,773, Oct. 9, 1985, which is a continuation of Ser. No. 553,157, Nov. 18, 1983, abandoned.

[51] Int. Cl.[4] .................. A61K 31/415; C07D 471/04; C07D 215/38
[52] U.S. Cl. .................................... 514/293; 514/237; 514/238; 544/126; 546/82; 546/159
[58] Field of Search .................. 546/82, 159; 544/126; 514/238, 237, 293

[56] References Cited

U.S. PATENT DOCUMENTS 4,013,665  3/1977  Crenshaw et al. .................... 546/82
4,052,393 10/1977  Treuner .............................. 260/250
4,191,766  3/1980  Warner et al. ...................... 424/250
4,197,403  4/1980  Warner et al. ...................... 544/346
4,525,584  6/1985  Gallick-Whitaker ................. 546/82

OTHER PUBLICATIONS

European Patent Application 0107455.
Derwent Abstract for Hungarian Application 2103/83 and the Hungarian Application.
Derwent Abstract for Portuguese Application 76045 and the Portuguese Application.
European Patent Application 093 593.

Primary Examiner—Henry R. Jiles
Assistant Examiner—J. Richter
Attorney, Agent, or Firm—Donald M. Sell; James A. Smith; Robert W. Sprague

[57] ABSTRACT

1H-imidazo[4,5-c]quinoline which are bronchodilators. Pharmacological methods of using the compounds as bronchodilators, pharmaceutical compositions containing the compounds, and synthetic intermediate for preparing the compounds are also described.

10 Claims, No Drawings

1H-IMIDAZO[4,5-c]QUINOLINES AND THEIR USE AS BRONCHODILATING AGENTS

CROSS-REFERNCE TO RELATED APPLICATION

This application is a continuation-in-part of copending application U.S. Ser. No. 785,773, filed Oct. 9, 1985, which is a continuation of U.S. Ser. No. 553,157 filed Nov. 18, 1983, and now abandoned.

TECHNICAL FIELD

This invention relates to certain 1H-imidazo[4,5-c]quinoline compounds. Pharmacological methods of using such compounds as bronchodilator agents, pharmaceutical compositions containing such compounds and intermediates for preparing such compounds are also included within the scope of the invention.

BACKGROUND OF THE INVENTION

The earliest report of an imidazo[4,5-c]quinoline ring system was by Backeberg et al, J. Chem. Soc., 972–977 (1938). However, his report of 4-methyl-1H-imidazo[4,5-c]quinoline and 2,4-dimethyl-1H-imidazo[4,5-c]quinoline (named as 2-methyl-quin(3:4:5':4')iminazole and 2:2'-dimethylquin(3:4:5':4')iminazole) is known to be erroneous in view of later work of Koenigs and Freund, Chemische Berichte 80, 143 (1947).

A further report by Backeberg, J. Chem. Soc., 1083–1089 (1938) of 2,4-dimethyl-3-phenyl-3H-imidazo[4,5-c]quinoline (named 1'-phenyl-2:2'-dimethylquin(3:4:5':4')iminazole) is also known to be erroneous in view of the above work of Koenigs and Freund.

The first reliable report of a 1H-imidazo[4,5-c]quinoline is by Bachman et al., J. Org. Chem. 15, 1278–1284 (1950) who synthesized 1-(6-methoxy-8-quinolinyl)-2-methyl-1H-imidazo[4,5-c]quinoline as a possible antimalarial agent.

Surrey et al, J. Am. Chem. Soc. 73, 2413 (1951) synthesized certain 3-nitro- and 3-amino-4-dialkylaminoalkylaminoquinolines as possible antimalarial and antibacterial agents.

Jain et al., J. Med. Chem. 11, pp. 87–92, (1968), synthesized the compound 1-[2-(4-piperidyl)ethyl]-1H-imidazo[4,5-c]quinoline as a possible anticonvulsant and cardiovascular agent.

Baranov et al., Chem. Abs. 85, 94362 (1976), reported several 2-oxoimidazo[4,5-c]quinolines.

Abbasi et al., Monatsh. Chem. 111 (4), pp 963–969 (1980), reported certain 2H-3-hydroxyimidazo[4,5-c]quinolines.

Berenyi et al, J. Heterocyclic Chem. 18, 1537–1540 (1981), reported certain 2-oxoimidazo[4,5-c]quinolines.

U.S. Pat. No. 3,700,674 (Diehl et al.) describes certain 4-alkylamino-3-nitroquinolines as herbicidal compounds.

DETAILED DESCRIPTION OF THE INVENTION

This invention relates to 1H-imidazo[4,5-c]quinolines which are useful bronchodilators. This invention also relates to pharmacological methods of using such compounds, pharmaceutical compositions containing such compounds and synthetic intermediates for preparing such compounds.

More specifically, this invention relates to novel bronchodilator compounds of Formula I

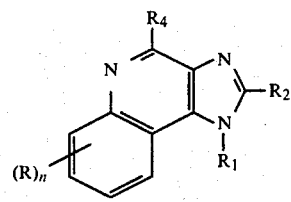

wherein $R_1$ is selected from the group consisting of hydrogen, alkyl of one to about ten carbon atoms, hydroxyalkyl of one to about six carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkyl alkanoate wherein the alkyl moiety contains one to about four carbon atoms and the alkanoate moiety contains two to about four carbon atoms, alkoxy of one to about four carbon atoms and halogen, with the proviso that when the benzene ring is substituted by two of said moieties, then the moieties together contain no more than 6 carbon atoms; $R_2$ is selected from the group consisting of hydrogen, trifluoromethyl, hydroxyalkyl of one to about six carbon atoms, aminoalkyl of one to about four carbon atoms, alkanamidoalkyl wherein each alkyl radical is one to about four carbon atoms, benzylthio, mercapto, alkylthio of one to about four carbon atoms, and alkyl of one to about eight carbon atoms, with the proviso that when $R_2$ is mercapto and $R_1$ is alkyl, $R_1$ is alkyl of one to four carbon atoms; $R_4$ is selected from the group consisting of hydrogen, chloro, alkyl of one to about four carbon atoms, alkoxy of one to about four carbon atoms, hydroxy, alkylamino of one to about four carbon atoms, dialkylamino wherein each alkyl radical contains one to about four carbon atoms, phenylthio, alkylthio of one to about four carbon atoms, and morpholino, with the proviso that when $R_2$ is mercapto, alkylthio or benzylthio, $R_4$ is hydrogen or alkyl; and each R is independently selected from the group consisting of alkoxy of one to about four carbon atoms, alkyl of one to about four carbon atoms, and halogen, and n is an integer from 0 to 2, with the proviso that when n is 2, then the R substituents together contain no more than 6 carbon atoms; and pharmaceutically acceptable acid addition salts thereof. Some of the compounds of Formula I are also useful antiviral agents.

In another aspect, this invention also relates to novel compounds of the formula

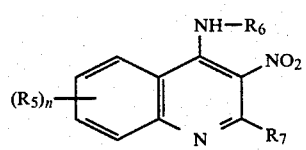

wherein each $R_5$ is independently selected from the group consisting of alkyl of one to about four carbon atoms, alkoxy of one to about four carbon atoms and halogen, and n is an integer from 0 to 2, with the proviso that when n is 2, then the $R_5$ substituents together contain no more than 6 carbon atoms; $R_6$ is selected from the group consisting of hydroxyalkyl of one to about six carbon atoms and cyclohexylmethyl; and R₇ is selected from the group consisting of alkyl of one to about four carbon atoms and hydrogen.

In still another aspect, this invention relates to novel compounds of the formula

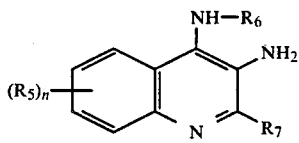

XXI wherein each R₅ is independently selected from the group consisting of alkyl of one to about four carbon atoms, alkoxy of one to about four carbon atoms and halogen, and n is an integer from 0 to 2, with the proviso that when n is 2, then the R₅ substituents together contain no more than 6 carbon atoms; R₆ is selected from the group consisting of hydroxyalkyl of one to about six carbon atoms and cyclohexylmethyl; and R₇ is selected from the group consisting of alkyl of one to about four carbon atoms and hydrogen.

In still another aspect, this invention relates to novel compounds of the formula

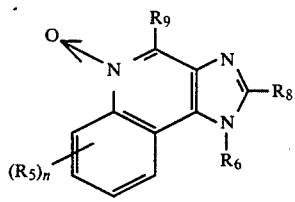

XXII wherein R₆ is selected from the group consisting of alkyl of one to about ten carbon atoms, hydroxyalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl-)ethyl and phenyl, the benzyl, (phenyl)ethyl or phenyl substituent being optionally substituted on the benzene ring by one or two moieties independently selected from the group consisting of alkyl of one to about four carbon atoms, alkyl alkanoate wherein the alkyl moiety contains one to about four carbon atoms and the alkanoate moiety contains two to about four carbon atoms, alkoxy of one to about four carbon atoms and halogen, with the proviso that if the benzene ring is substituted by two of said moieties, then said moieties together contain no more than 6 carbon atoms; R₈ is selected from the group consisting of hydrogen, trifluoromethyl, hydroxyalkyl of one to about six carbon atoms, aminoalkyl of one to about four carbon atoms, alkyl of one to about eight carbon atoms and alkanamidoalkyl wherein each alkyl radical is one to about four carbon atoms; R₉ is hydrogen or methyl; and each R₅ is independently selected from the group consisting of halogen, alkoxy of one to about four carbon atoms, and alkyl of one to about four carbon atoms, and n is an integer from 0 to 2, with the proviso that if n is 2, then the R₅ substituents together contain no more than 6 carbon atoms.

The compounds of Formula XX, XXI, and XXII are useful intermediates in the preparation of the compounds of Formula I. Further, certain of the compounds of Formulas I, XX, XXI, and XXII are useful intermediates for preparing the 1H-imidazo[4,5-c]quinolin-4-amines disclosed in copending U.S. Ser. No. 798,385 filed 11/15/85, now U.S. Pat. No. 4,689,338 and commonly assigned, and incorporated herein by reference. The compounds of said copending application exhibit useful antiviral activity.

Some of the compounds of Formula I are aryl or alkyl amines and those that are may be used in the form of acid addition salts such as hydrochlorides, dihydrogen sulfates, trihydrogen phosphates, hydrogen nitrates, methane sulfonates and salts of other pharmaceutically acceptable acids. Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble, an example of such a solvent being diethyl ether.

Generally, alkyl moieties which may be contained in the compounds of the invention may be straight or branched-chain or cyclic.

R₁ (Formula I) and R₆ (Formulas XX, XXI, and XXII) substituents which are alkyl preferably contain one to about eight carbon atoms, and more preferably contain about four to about six carbon atoms.

R₂ (Formula I) and R₈ (Formula XXII) substituents which are alkyl preferably contain one to about four carbon atoms.

Hydroxyalkyl substituents which may be contained in the compounds of the invention preferably contain one to about four carbon atoms.

The remaining substituents which may be contained in the compounds of the invention and contain an alkyl radical such as the substituents alkoxy, aminoalkyl, alkylthio, alkylamino, dialkylamino and alkyl (other than R₁, R₆, R₂ and/or R₈ as alkyl) preferably contain one or two carbon atoms in each alkyl radical.

The preferred cyclic alkyl moieties contain six or seven carbon atoms.

The halogen substituents which may be contained in the compounds of the instant invention are selected from fluorine, chlorine and bromine. Preferred halogen substituents are fluorine and chlorine.

It is preferred that n of Formulas I, XX, XXI, and XXII be zero or one. It is most preferred that n of Formulas I, XX, XXI, and XXII be zero.

If R₁ of Formula I or R₆ of Formula XXII is substituted benzyl, (phenyl)ethyl or phenyl, it is preferred that the benzene ring be mono-substituted. It is most preferred that the benzyl, (phenyl)ethyl or phenyl substituent be unsubstituted. As used in the instant specification and claims, "(phenyl)ethyl" denotes 1-(phenyl-)ethyl or 2-(phenyl)ethyl.

It is presently preferred that R₁ of Formula I be alkyl, benzyl, (phenyl)ethyl, cyclohexylmethyl or hydroxyalkyl. When R₁ of Formula I is cyclic alkyl, it is preferably cyclohexylmethyl.

When R₁ of Formula I is hydroxyalkyl, the compounds of the invention may contain from one to three hydroxy substituents. Preferred hydroxyalkyl groups contain one or two hydroxy substituents.

Presently preferred bronchodilator compounds of Formula I are:
4-chloro-1-methyl-1H-imidazo[4,5-c]quinoline,
1,8-dimethyl-2-hydroxymethyl-1H-imidazo[4,5-c]quinoline, 1,8-dimethyl-2-trifluoromethyl-1H-imidazo[4,5-c]quinoline,
1-methyl-4-methoxy-1H-imidazo[4,5-c]quinoline,
1-isobutyl-8-methyl-1H-imidazo[4,5-c]quinoline, amino, phenylthio, alkylthio, morpholino or hydroxy are prepared by further reaction of intermediates of Formula vIII or IX as shown in the latter steps of the Reaction Scheme below.

Reaction Scheme A

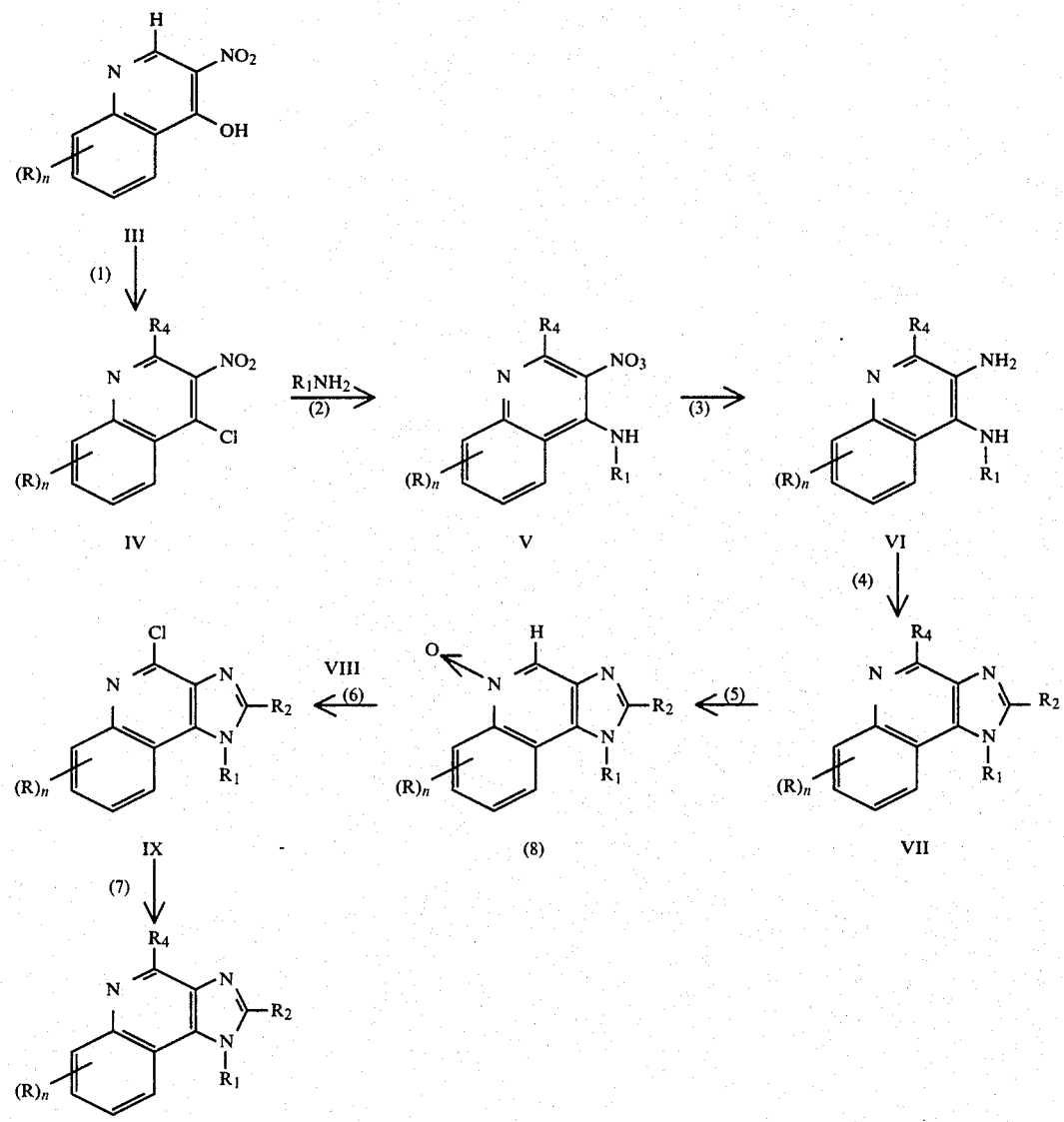

1-ethyl-2-methyl-1H-imidazo[4,5-c]quinoline,
1-ethyl-1H-imidazo[4,5-c]quinoline,
1-phenyl-1H-imidazo[4,5-c]quinoline,
1-(4-fluorophenyl)-1H-imidazo[4,5-c]quinoline,
1-isobutyl-1H-imidazo[4,5-c]quinolin-4-ol,
7,8-dimethoxy-1-isobutyl-1H-imidazo-[4,5-c]quinoline, and
7,8-dimethoxy-1-isobutyl-1H-imidazo[4,5-c]quinolin-4-ol.

The most preferred bronchodilator is above-mentioned 1-isobutyl-1H-imidazo[4,5-c]quinolin-4-ol.

Compounds of the invention of Formula I wherein $R_1$, $R_2$, R and n are as defined above, and $R_4$ is hydrogen or alkyl are prepared as described in the first three steps of the Reaction Scheme A below. Compounds of the invention of Formula I wherein $R_1$, $R_2$, R and n are as defined above, and $R_4$ is alkoxy, alkylamino, dialkyl- Many quinolines of Formula Iv are known compounds (see, e.g., U.S. Pat. No. 3,700,674 and references described therein). Those which are not may be prepared by known methods, for example, from 4-hydroxy-3-nitroquinolines as illustrated in step (1) of the Reaction Scheme. Step (1) may be conducted by reacting the 4-hydroxy-3-nitroquinoline of Formula III with phosphorus oxychloride. The reaction is preferably conducted in N,N-dimethylformamide and is accompanied by heating. A large molar excess of phosphorus oxychloride is preferably avoided. Employment of about a 1-2 molar ratio of phosphorus oxychloride to the 4-hydroxy-3-nitroquinoline has been found to be particularly suitable. Some compounds of Formula V are known such as those wherein $R_1$ is optionally substituted (phenyl)ethyl, 6-methoxy-8-quinolinyl, dialkylaminoalkyl, and phenyl. However, compounds of Formula V wherein $R_1$ is cyclohexylmethyl or hydroxyalkyl are novel.

In step (2), an optionally substituted 3-nitro-4-chloroquinoline of Formula IV wherein $R_4$ is hydrogen or alkyl is reacted by heating with an amine of the formula $R_1NH_2$ in a suitable solvent such as water or tetrahydrofuran to provide a quinoline of Formula V wherein $R_4$ is hydrogen or alkyl.

Steps (1) and (2) may be combined such that the 3-nitro-4-chloroquinoline need not be isolated prior to reaction with the amine. Such a reaction is exemplified in Example 167 and Example 239 (Step A) below.

Compounds of Formula V are catalytically reduced in step (3) using a platinum catalyst such as platinum on charcoal to provide compounds of Formula VI wherein $R_4$ is hydrogen or alkyl. The reduction is conveniently carried out on a Parr apparatus in a non-reactive solvent such as toluene or a lower alkanol. Compounds of Formula VI wherein $R_1$ is cyclohexylmethyl or hydroxyalkyl are novel.

In step (4) the intermediate compounds of Formula VI are reacted with a dialkoxyalkyl alkanoate such as diethoxymethyl acetate, or a carboxylic acid which can introduce the desired $R_2$ group, or a trialkyl ortho ester of the formula $R_2C(Oalkyl)_3$, wherein "alkyl" is an alkyl group containing 1 to about 8 carbon atoms, or the combination of such a trialkyl ortho ester and such a carboxylic acid to provide a novel compound of Formula YII, which is a subgroup of the compounds of Formula I wherein $R_4$ is hydrogen or alkyl. The reaction of step (4) is carried out by heating, e.g., at about 130° C., in the presence of an acid, preferably an alkanoic acid having one more carbon atom than $R_2$. Suitable acids also include haloalkanoic acids, aminoalkanoic acids, hydroxyalkanoic acids and the like. Carbon disulfide may also be used in the presence of strong base to provide compounds wherein $R_2$ is -SH. The compounds of Formula VII are active as bronchodilators. In addition, compounds of Formula VII wherein $R_4$ is hydrogen are particularly useful as intermediates to provide other compounds of Formula I as described below.

When $R_4$ is H, step (5) provides a novel intermediate of Formula VIII through oxidation of the compound of Formula VII with a typical oxidizing agent used to form N-oxides. Suitable oxidizing agents include peracids and hydrogen peroxide. The oxidation reaction is preferably conducted in glacial acetic acid. Heating is generally employed to accelerate the rate of reaction.

Steps (4) and (5) may be combined such that the compound of Formula VII need not be isolated prior to reaction with the oxidizing agent. Such a reaction is exemplified in Example 238 (Step C) below.

In step (6) the N-oxide of Formula VIII is converted to the 4-chloro intermediate of Formula IX by heating in the presence of a suitable chlorinating agent such as phosphorus oxychloride. It is preferred that phosphorus oxychloride be used in combination with N,N-dimethylformamide as the solvent.

In step (7) the 4-chloro group of the compound of Formula IX is replaced with alkoxy, alkylamino, dialkylamino, phenylthio, alkylthio, or morpholino by reacting the compound of Formula IX with an alkoxide, an alkylamine, a dialkylamine, phenylthiol, an alkanethiol, or morpholine, respectively to provide a compound of the invention of Formula X. The reaction is carried out by heating the reactants, generally at reflux, in an inert solvent. In order to prepare compounds of Formula X wherein $R_4$ is —OH, an intermediate of Formula VIII is heated with acetic anhydride as shown in step (8).

Compounds of Formula I of the invention wherein $R_2$ is alkanamidoalkyl are prepared by acylation of compounds wherein $R_2$ is aminoalkyl. Compounds of Formula I of the invention wherein $R_2$ is alkythio or benzylthio are prepared by alkylation or benzylation of the corresponding mercapto compound.

For compounds wherein Rl of Formula I is hydroxyalkyl, the synthesis illustrated in the Reaction Scheme A above is preferably modified. Specifically, it is generally necessary to first block or protect the hydroxy group with an acyloxy group such as alkanoyloxy or benzoyloxy for step(s) (5) and/or (6) and/or (7), and to then remove the blocking group. Such blocking reactions are exemplified in Examples 118-121, 123-126 and 133 below.

The bronchodilator activity of the compounds of Formula I was assessed by the measurement of effects on isolated tracheal spirals. This is a well-known and conventional test method. The in vitro bronchodilator activity was determined as follows: Female guinea pigs were sacrificed, and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in $\mu g/ml$) required to provide greater than 75% relaxation of the drug induced contraction is considered an effective concentration. For comparision, a well known standard bronchodilator, aminophylline, requires concentrations of 50 $\mu g/ml$ versus histamine, 100 $\mu g/ml$ versus acetylcholine and 10 $\mu g/ml$ versus barium chloride to provide greater than 75% relaxation of the drug induced contraction.

The compounds of Formula I may be administered to mammals in order to obtain bronchodilation. The compounds may be administered orally, parenterally or by inhalation. The usual effective dose will be 0.1 to 50 mg/kg of body weight. Preferably, they are administered orally.

The compounds of Formula I, or their pharmaceutically acceptable acid-addition salts, can be combined with conventional pharmaceutically-acceptable diluents and carriers to form such dosage forms as tablets, capsules, suspensions, solutions, suppositories and the like to provide useful bronchodilator compositions.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

Some of the compounds of Formula I also have antiviral activity including:
1,8-dimethyl-8-fluoro-1H-imidazo[4,5-c]quinoline, 1-methyl-4-(4-morpholino)-1H-imidazo[4,5-c]quinoline,
1,8-dimethyl-1H-imidazo[4,5-c]quinoline,
1,8-dimethyl-2-hydroxymethyl-1H-imidazo[4,5-c]quinoline,
1-methyl-4-methoxy-1H-imidazo[4,5-c]quinoline,
2-(3-aminopropyl)-1,8-dimethyl-1H-imidazo[4,5-c]quinoline,
N-(n-butyl)-1-methyl-1H-imidazo[4,5-c]quinolin-4-amine,
1-(2,3-dihydroxypropyl)-N-methyl-1H-imidazo[4,5-c]quinolin4-amine,
1-ethyl-2-methyl-1H-imidazo[4,5-c]quinoline,
2-benzylthio-1-methyl-1H-[4,5-c]quinoline,
1-isobutyl-2-mercapto-1H-imidazo[4,5-c]quinoline,
1-(2,3-dihydroxypropyl)-4-methoxy-1H-imidazo[4,5-c]quinoline, and
4-chloro-1-(4-methoxyphenyl)-1H-imidazo[4,5-c]quinoline. The preferred antiviral compounds of Formula I are: 1,2-dimethyl-1H-imidazo[4,5-c]quinoline, 1-benzyl-2-methyl-1H-imidazo[4-5c]quinoline, and 1,2,8-trimethyl-1H-imidazo[4,5-c]quinoline.

The antiviral activity of such compounds of Formula I is preferably demonstrated using the method described generally by Kern, et al., Antimicrob. Agents Chemother. 14, 817–823 (1978).

This method uses female guinea pigs of 200 to 300 grams in weight, preferably 200 to 250 grams in weight. The preferred strain of pigs is Hartley. The pigs are anesthetized with pentobarbital or methoxyflurane, and are then infected with about $10^5$ plaque forming units of Type II Herpes simplex virus type intravaginally using a cotton swab. Type I Herpes simplex virus may also be used in this screening method. Drugs are prepared in saline or in water using a surfactant such as "Tween 80" (a polyoxyethylene sorbitan monooleate commercially available from Emulsion Engineering, Inc., Elk Grove village, Illinois). Alternatively, the compounds of Formula I may be formulated in "PEG 400" (a polyethylene of average molecular weight of about 400, commercially available from Union Carbide Corporation) or in a polyethylene glycol cream. The drugs are applied intravaginally, for example, twice daily for a predetermined number of days, for example, five days. Application is initiated at a predetermined interval after infection such as one hour after infection. Virus replication can be monitored by determining the amount of virus recovered with vaginal swabs taken, for example, on days 1, 2, 3, 5 or 7 after infection. virus is eluted from the swab in 1 ml of cell growth medium (Medium 199, Gibco Laboratories, Grand Island, N.Y.) and virus titer is determined using cell monolayers. External lesions are scored daily for 10 days using the following scale: zero, no lesion; 1, redness or swelling; 2, a few small vesicles; 3, several large vesicles; 4, large ulcers and necrosis; 5, paralysis. Percent inhibition of lesion development is determined by comparing untreated, but infected control animals and drug treated animals. Comparison with known drugs such as phosphonacetic acid and acyclovir may also be undertaken.

In the antiviral method of the invention, active compounds of Formula I are used to control Type I or Type II Herpes simplex virus by applying to a population thereof an amount of a compound sufficient to attain said control.

The method of the invention is preferably used in vivo for treating infections caused by the viruses, especially in mammals. By "active" virus is meant non-dormant virus. The method is generally effective when a compound of the invention or its formulation is administered topically (e.g., intravaginally or on the skin), for example, to a genital herpes infection.

The antiviral compounds of Formula I are formulated for the various routes of administration in known, pharmaceutically acceptable vehicles such as water or polyethylene glycol, generally, the compound of Formula I being present in an amount of less than about 10% by weight, and preferably about 0.1–5% by weight. Such compounds of Formula I are preferably administered in water with either a surfactant such as "Tween 80" discussed above or cellulose.

The following examples are provided to illustrate the invention and are not intended to be limiting thereof.

EXAMPLE 1

Preparation of a Compound of Formula V

To a stirred solution of 50.0 g (0.24 mole) of 4-chloro-3-nitroquinoline in 300 ml of tetrahydrofuran was added, in small portions, 52.7 g (0.72 mole) of isobutylamine. The mixture was heated at its reflux temperature for one hour and was then evaporated in vacuo. Water was added to the residue, and the solid was separated by filtration. The solid was suspended in one liter of water, and was dissolved by the gradual addition of concentrated hydrochloric acid (to pH 3 to 4) followed by filtration of the solution. The filtrate was basified (to pH 9 to 10) by the addition of concentrated ammonium hydroxide to provide bright yellow 4-(isobutylamino)-3-nitroquinoline, m.p. 119°–121° C. The structural assignment was supported by infrared spectral analysis.

EXAMPLE 2

Alternative Preparation of a Compound of Formula V

To a stirred solution of 40% aqueous methylamine was added, in small portions, 30.0 g (0.144 mole) of 4-chloro-3-nitroquinoline. The reaction mixture was then heated at its reflux temperature for about 0.75 hour. After cooling, the mixture was poured in 300 ml of water. The solid was separated by filtration, and was then suspended in 300 ml of water. Acidification with 6N hydrochloric acid to pH 3 to 4 effected dissolution of most of the solid. Filtration was followed by basification of the filtrate with concentrated ammonium hydroxide to pH 8 to 10 to provide a yellow precipitate. The solid was separated by filtration, washed with water, and recrystallized from ethanol to provide yellow 4-methylamino-3-nitroquinoline, m.p. 168°–170° C. Analysis: Calculated for $C_{10}H_9N_3O_2$ %C, 59.1; %H, 4.5; %N, 20.7; Found: %C, 59.0; %H, 4.2; %N, 20.8.

Using the methods of Examples 1 and 2, and starting with the indicated substituted quinolines and primary amines, the following compounds of Formula V were prepared (Table I):

TABLE I

| Ex. No. | Quinoline Starting Material of Formula IV | Primary Amine Starting Material | Intermediate of Formula V (m.p. in °C.) |
|---|---|---|---|
| 3 | 4,6-dichloro-3-nitroquinoline | methylamine | 6-chloro-4-methylamino-3-nitroquinoline |

TABLE I-continued

| Ex. No. | Quinoline Starting Material of Formula IV | Primary Amine Starting Material | Intermediate of Formula V (m.p. in °C.) |
|---|---|---|---|
| 4 | 4-chloro-3-nitro-quinoline | ethanolamine | 4-(2-hydroxyethylamino)-3-nitroquinoline (204–207) |
| 5 | 4-chloro-3-nitro-quinoline | 2,3-dihydroxy-propylamine | 4-(2,3-dihydroxypropyl-amino)-3-nitroquinoline (209–211) |
| 6 | 4-chloro-3-nitro-quinoline | ethylamine | 4-ethylamino-3-nitro-quinoline (145–148) |
| 7 | 4-chloro-6-methyl-3-nitroquinoline | methylamine | 6-methyl-4-methylamino-3-nitroquinoline (168–171) |
| 8 | 4-chloro-6-methyl-3-nitroquinoline | isobutylamine | 4-isobutylamino-6-methyl-3-nitroquinoline (108–110) |
| 9 | 4-chloro-6-fluoro-3-nitroquinoline | methylamine | 6-fluoro-4-methylamino-3-nitroquinoline (198–202) |
| 10 | 4,7-dichloro-3-nitroquinoline | isobutylamine | 7-chloro-4-isobutylamino-3-nitroquinoline (not taken) |
| 11 | 4-chloro-3-nitro-quinoline | aniline | 3-nitro-4-phenylamino-quinoline (129–132) |
| 12 | 4-chloro-3-nitro-quinoline | 4-methoxyaniline | 4-(4-methoxyphenylamino)-3-nitroquinoline (136–138) |
| 13 | 4-chloro-3-nitro-quinoline | 4-fluoroaniline | 4-(4-fluorophenylamino)-3-nitroquinoline (147–151) |
| 14 | 4-chloro-3-nitro-quinoline | ammonia | 4-amino-3-nitroquinoline (263–265) |
| 15 | 4-chloro-3-nitro-quinoline | n-butylamine | 4-(n-butylamino)-3-nitroquinoline (81–83) |
| 16 | 4-chloro-3-nitro-quinoline | 3-hydroxypropyl-amine | 4-(3-hydroxypropylamino)-3-nitroquinoline (159–162) |
| 17 | 4-chloro-6-fluoro-2-methyl-3-nitro-quinoline | 2,3-dihydroxy-propylamine | 4-(2,3-dihydroxypropyl-amino)-6-fluoro-2-methyl-3-nitroquinoline (187–189) |
| 18 | 4-chloro-6-fluoro-2-methyl-3-nitro quinoline | ammonia | 4-amino-6-fluoro-2-methyl 3-nitroquinoline (143–158) |
| 19 | 4-chloro-6-fluoro-2-methyl-3-nitro-quinoline | methylamine | 6-fluoro-2-methyl-4-methylamino-3-nitro-quinoline (182–184) |
| 20 | 4-chloro-6-fluoro-2-methyl-3-nitro-quinoline | benzylamine | 4-benzylamino-6-fluoro-2-methyl-3-nitroquino-line (171–174) |
| 21 | 4-chloro-3-nitro-quinoline | 2-(N,N—dimethyl-amino)ethylamine | 4-[2-(N,N—dimethyl-amino)ethylamino]-3-nitroquinoline (124–145) |
| 22 | 4-chloro-3-nitro-quinoline | ethyl 4-amino-phenylacetate | ethyl 4-(3'-nitro-4'-quinolinyl)-aminophenylacetate (104–106) |
| 23 | 4-chloro-3-nitro-quinoline | 4-chlorobenzylamine | 4-(4-chlorobenzyl-amino)-3-nitroquinoline (not taken) |
| 24 | 4-chloro-3-nitro-quinoline | 2-methoxyethylamine | 4-(2-methoxyethylamino)-3-nitroquinoline (115–118) |
| 25 | 4-chloro-6-methyl-3-nitroquinoline | n-butylamine | 4-(n-butylamino)-6-methyl-3-nitroquinoline (not taken) |

EXAMPLE 26

Preparation of a Compound of Formula VI

To a solution of 57.3 g (0.23 mole) of 4-(isobutylamino)-3-nitroquinoline (from Example 1) in 600 ml of ethanol was added about 2 g of platinum on charcoal, and the resulting mixture was hydrogenated on a Parr apparatus for three hours. Filtration followed by evaporation in vacuo provided a residue which gradually solidified to yellow solid 3-amino-4-(isobutylamino)quinoline.

Using the method of Example 26, and starting with the indicated intermediates of Formula V, the intermediates of Formula VI shown in Table II were prepared. In those cases where the hydrochloride is listed, it was obtained by first bubbling hydrogen chloride through an ethanol solution of the free amine and then separating the solid product by filtration.

TABLE II

| Ex. No. | Intermediate of Formula V (Example No.) | Intermediate of Formula VI (m.p. in °C.) |
|---|---|---|
| 27 | 2 | 3-amino-4-(methylamino)quinoline hydrochloride (294-296) |
| 28 | 3 | 3-amino-6-chloro-4-(methylamino)-quinoline (not taken) |
| 29 | 4 | 3-amino-4-(2-hydroxyethylamino)-quinoline dihydrochloride (282-283) |
| 30 | 5 | 3-amino-4-(2,3-dihydroxypropyl-amino)quinoline hydrochloride (201-204) |
| 31 | 6 | 3-amino-4-(ethylamino)quinoline hydrochloride (226-229) |
| 32 | 7 | 3-amino-6-methyl-4-(methylamino)-quinoline hydrochloride (>300) |
| 33 | 8 | 3-amino-4-isobutylamino-6-methyl-quinoline (not taken) |
| 34 | 9 | 3-amino-6-fluoro-4-(methylamino)-quinoline (not taken) |
| 35 | 10 | 3-amino-7-chloro-4-(isobutylamino)-quinoline (not taken) |
| 36 | 11 | 3-amino-4-phenylaminoquinoline (not taken) |
| 37 | 12 | 3-amino-4-(4-methoxyphenylamino)-quinoline (not taken) |
| 38 | 13 | 3-amino-4-(4-fluorophenylamino)-quinoline (not taken) |
| 39 | 14 | 3,4-diaminoquinoline (170-174) |
| 40 | 15 | 3-amino-4-(n-butylamino)quinoline (80-83) |
| 41 | 16 | 3-amino-4-(3-hydroxypropylamino)-quinoline (not taken) |
| 42 | 17 | 3-amino-4-(2,3-dihydroxypropyl-amino)-6-fluoro-2-methylquinoline (tan solid) (not taken) |
| 43 | 18 | 3,4-diamino-6-fluoro-2-methyl-quinoline (not taken) |
| 44 | 19 | 3-amino-6-fluoro-2-methyl-4-methylaminoquinoline (123-131) |
| 45 | 20 | 3-amino-4-benzylamino-6-fluoro-2-methylquinoline (not taken) |
| 46 | 21 | 3-amino-4-[2-(N,N—dimethylamino)ethylamino]quinoline (not taken) |
| 47 | 22 | ethyl 4-(3-amino-4-quinolinyl)-aminophenylacetate (not taken) |
| 48 | 23 | 3-amino-4-(4-chlorobenzylamino)-quinoline (not taken) |

EXAMPLE 49

Preparation of a Compound of Formula VII

Crude 3-amino-4-(methylamino)quinoline (0.207 mole) obtained by the method of Example 26 was mixed with 500 ml of glacial acetic acid and 76 ml of triethyl orthoacetate, and the resulting mixture was heated at reflux for two hours. Evaporation provided a residue which was dissolved in 800 ml of water. The solution was basified with concentrated ammonium hydroxide. The solid was separated by filtration and washed with water to provide 1,2-dimethyl-1H-imidazo[4,5-c]quinoline. When a sample of this product was recrystallized from diethyl ether, it had a melting point of 194°–196° C. Analysis: Calculated for $C_{12}H_{11}N_3$: %C, 73.1; %H, 5.6; %N, 21.3; Found: %C, 73.4; %H, 5.7; %N, 21.5.

Using the method of Example 49, and starting with the indicated intermediates, carboxylic acids and trialkyl orthoesters, the compounds of Formula VII shown in Table III were prepared.

TABLE III

| Ex. No. | Intermediate of Formula VI (Example No.) | Ortho Ester; Carboxylic Acid | Compound of Formula VII (m.p. in °C.) |
|---|---|---|---|
| 50 | 26 | triethyl orthoformate; formic acid | 1-isobutyl-1H—imidazo[4,5-c]quinoline (92-95) |
| 51 | 28 | triethyl orthoacetate; acetic acid | 8-chloro-1,2-dimethyl-1H—imidazo[4,5-c]quinoline (not taken) |
| 52 | 29 | triethyl orthoformate; formic acid | 1-(2-hydroxyethyl)-1H—imidazo[4,5-c]-quinoline (170-172) |
| 53 | 30 | triethyl orthoacetate; acetic acid | 1-(2,3-dihydroxypropyl)-2-methyl-1H—imidazo[4,5-c]quinoline (232-234) |
| 54 | 31 | triethyl orthoacetate; acetic acid | 1-ethyl-2-methyl-1H—imidazo[4,5-c]-quinoline (126-129) |
| 55 | 32 | triethyl orthoformate; formic acid | 1,8-dimethyl-1H—imidazo[4,5-c]-quinoline hydrate (180-184) |
| 56 | 32 | triethyl orthoacetate; acetic acid | 1,2,8-trimethyl-1H—imidazo[4,5-c]-quinoline (220-221) |
| 57 | 31 | triethyl orthoformate; formic acid | 1-ethyl-1H—imidazo[4,5-c]quinoline (80-82) |
| 58 | 33 | triethyl orthoformate; formic acid | 1-isobutyl-8-methyl-1H—imidazo[4,5-c]quinoline (160-163) |
| 59 | 34 | triethyl orthoformate; formic acid | 8-fluoro-1-methyl-1H—imidazo[4,5-c]-quinoline hydrate (201-205) |
| 60 | 35 | triethyl orthoformate; formic acid | 7-chloro-1-isobutyl-1H—imidazo[4,5-c]-quinoline (not taken) |
| 61 | 36 | triethyl orthoformate; formic acid | 1-phenyl-1H—imidazo[4,5-c]quinoline (137-139) |

TABLE III-continued

| Ex. No. | Intermediate of Formula VI (Example No.) | Ortho Ester; Carboxylic Acid | Compound of Formula VII (m.p. in °C.) |
|---|---|---|---|
| 62 | 37 | triethyl orthoformate; formic acid | 1-(4-methoxyphenyl)-1H—imidazo[4,5-c]quinoline (150–152) |
| 63 | 38 | triethyl orthoacetate; acetic acid | 1-(4-fluorophenyl)-2-methyl-1H—imidazo[4,5-c]quinoline (191–193) |
| 64 | 37 | triethyl orthoacetate; acetic acid | 1-(4-methoxyphenyl)-2-methyl-1H—imidazo[4,5-c]quinoline (174–176) |
| 65 | 38 | triethyl orthoformate; formic acid | 1-(4-fluorophenyl)-1H—imidazo[4,5-c]quinoline (159–161) |
| 66 | 39 | triethyl orthoformate; formic acid | 1H—imidazo[4,5-c]quinoline hydrate (>250) |
| 67 | 40 | triethyl orthoformate; formic acid | 1-(n-butyl)-1H—imidazo[4,5-c]quinoline (not taken) |
| 68 | 41 | triethyl orthoformate; formic acid | 1-(3-hydroxypropyl)-1H—imidazo[4,5-c]quinoline (not taken) |
| 69 | 27 | triethyl orthoformate; formic acid | 1-methyl-1H—imidazo[4,5-c]quinoline (143–145) |
| 70 | 30 | triethyl orthoformate; formic acid | 1-(2,3-dihydroxypropyl)-1H—imidazo[4,5-c]quinoline (228–230) |
| 71 | 26 | triethyl orthoacetate; acetic acid | 1-isobutyl-2-methyl-1H—imidazo[4,5-c]quinoline hydrate (85–88) |
| 72 | 34 | triethyl orthoacetate; acetic acid | 1,2-dimethyl-8-fluoro-1H—imidazo[4,5-c]quinoline (234–239) |
| 73 | 47 | triethyl orthoformate; formic acid | ethyl 4-(1-1H—imidazo[4,5-c]quinolinyl)phenylacetate (105–109) |

EXAMPLE 74

Preparation of a Compound of Formula VIII

To a solution of 9.3 g (0.0413 mole) of 1-isobutyl-1H-imidazo[4,5-c]quinoline (from Example 50) in 150 ml of acetic acid was added 1.5 equivalents (0.062 mole) of 30% hydrogen peroxide. The mixture was heated at 65°–70° C. for one day, and was then evaporated. The residue was neutralized with saturated sodium bicarbonate solution and the resulting mixture was extracted with dichloromethane. The extracts were dried, then evaporated to provide a residue which solidified gradually to yellow solid 1-isobutyl-1H-imidazo[4,5-c]quinolin-5-oxide. This product was recrystallized twice from ethyl acetate to give a green solid, m.p. 211°–213° C. Analysis: Calculated for $C_{14}H_{15}N_3O$: %C, 69.7; %H, 6.3; %N, 17.4; Found: %C, 69.7; %H, 6.3, %N, 17.1.

Using the method of Example 74, and starting with the indicated intermediates, the compounds of Formula VIII shown in Table IV were prepared.

TABLE IV

| Ex. No. | Compound of Formula VII (Example No.) | Compound of Formula VIII (m.p. in °C.) |
|---|---|---|
| 75 | 51 | 8-chloro-1,2-dimethyl-1H—imidazo[4,5-c]quinolin-5-oxide (not taken) |
| 76 | 127 (Part C) | 1-benzyl-1H—imidazo[4,5-c]quinolin-5-oxide (241–251) |
| 77 | 128 (Part C) | 1-cyclohexylmethyl-1H—imidazo[4,5-c]quinolin-5-oxide (224–226, dec.) |
| 78 | 54 | 1-ethyl-2-methyl-1H—imidazo[4,5-c]quinolin-5-oxide (220–222) |
| 79 | 55 | 1,8-dimethyl-1H—imidazo[4,5-c]quinolin-5-oxide (265–268) |
| 80 | 56 | 1,2,8-trimethyl-1H—imidazo[4,5-c]quinolin-5-oxide (not taken) |
| 81 | 57 | 1-ethyl-1H—imidazo[4,5-c]quinolin-5-oxide (not taken) |
| 82 | 58 | 1-isobutyl-8-methyl-1H—imidazo[4,5-c]quinolin-5-oxide (not taken) |
| 83 | 59 | 8-fluoro-1-methyl-1H—imidazo[4,5-c]quinolin-5-oxide (not taken) |
| 84 | 60 | 7-chloro-1-isobutyl-1H—imidazo[4,5-c]quinolin-5-oxide (not taken) |
| 85 | 61 | 1-phenyl-1H—imidazo[4,5-c]quinolin-5-oxide (222–225) |
| 86 | 62 | 1-(4-methoxyphenyl)-1H—imidazo[4,5-c]quinolin-5-oxide (245–247) |
| 87 | 63 | 1-(4-fluorophenyl)-2-methyl-1H—imidazo[4,5-c]quinolin-5-oxide (245–248) |
| 88 | 64 | 1-(4-methoxyphenyl)-2-methyl-1H—imidazo[4,5-c]quinolin-5-oxide (211–213) |
| 89 | 65 | 1-(4-fluorophenyl)-1H—imidazo[4,5-c]quinolin-5-oxide (257–259) |
| 90 | 169 | 2-methyl-1-[2-(phenyl)ethyl]-1H—imidazo[4,5-c]quinolin-5-oxide (204–206) |
| 91 | 49 | 1,2-dimethyl-1H—imidazo[4,5-c]quinolin-5-oxide (234–237) |
| 92 | 69 | 1-methyl-1H—imidazo[4,5-c]quinolin-5-oxide (241–244) |
| 93 | 73 | ethyl 4-(1-1H—imidazo[4,5-c]quinolin-5-oxide)phenylacetate (not taken) |
| 94 | 71 | 1-isobutyl-2-methyl-1H—imidazo[4,5-c]quinolin-5-oxide (214–216) |
| 95 | 72 | 1,2-dimethyl-8-fluoro-1H—imidazo[4,5-c]- |

TABLE IV-continued

| Ex. No. | Compound of Formula VII (Example No.) | Compound of Formula VIII (m.p. in °C.) |
|---|---|---|
| | | quinolin-5-oxide (not taken) |

EXAMPLE 96

Preparation of a Compound of Formula IX

A mixture of 9.95 g (0.0412 mole) of 1-isobutyl-1H-imidazo[4,5-c]quinolin-5-oxide (from Example 74) and 100 ml of phosphorus oxychloride was heated at its reflux temperature for 2.5 hours, and was then cooled and poured into ice with stirring. Basification (to pH 9-10) with 50% aqueous sodium hydroxide solution was followed by extraction with dichloromethane. The extracts were dried over sodium chloride and sodium bicarbonate, and then evaporated to provide a solid residue. A sample of the residue was recrystallized from diethyl ether to provide 4-chloro-1-isobutyl-1H-imidazo[4,5-c]quinoline, m.p. 134°-136° C. Analysis: Calculated for $C_{14}H_{17}ClN_3$: %C, 64.7; %H, 5.4; %N, 16.2; Found: %C, 64.3; %H, 5.3; %N, 16.3.

Using the method of Example 96, and starting with the indicated compounds of Formula VIII, the compounds of Formula IX were prepared.

TABLE V

| Ex. No. | Compound of Formula VIII (Example No.) | Compound of Formula IX (m.p. in °C.) |
|---|---|---|
| 97 | 91 | 4-chloro-1,2-dimethyl-1H—imidazo[4,5-c]-quinoline (198-200) |
| 98 | 75 | 4,8-dichloro-1,2-dimethyl-1H—imidazo-[4,5-c]quinoline (not taken) |
| 99 | 76 | 1-benzyl-4-chloro-1H—imidazo[4,5-c]-quinoline (160-167) |
| 100 | 77 | 4-chloro-1-cyclohexylmethyl-1H—imidazo[4,5-c]quinoline (176-179) |
| 101 | 78 | 4-chloro-1-ethyl-2-methyl-1H—imidazo-[4,5-c]quinoline (170-172) |
| 102 | 79 | 4-chloro-1,8-dimethyl-1H—imidazo[4,5-c]-quinoline (233-237) |
| 103 | 80 | 4-chloro-1,2,8-trimethyl-1H—imidazo-[4,5-c]quinoline (243-247) |
| 104 | 81 | 4-chloro-1-ethyl-1H—imidazo[4,5-c]-quinoline (not taken) |
| 105 | 82 | 4-chloro-1-isobutyl-8-methyl-1H—imidazo[4,5-c]quinoline (202-205) |
| 106 | 83 | 4-chloro-8-fluoro-1-methyl-1H—imidazo-[4,5-c]quinoline (not taken) |
| 107 | 84 | 4,7-dichloro-1-isobutyl-1H—imidazo[4,5-c]quinoline (not taken) |
| 108 | 85 | 4-chloro-1-phenyl-1H—imidazo[4,5-c]-quinoline (not taken) |
| 109 | 86 | 4-chloro-1-(4-methoxyphenyl)-1H—imidazo-[4,5-c]quinoline (210-212) |
| 110 | 87 | 4-chloro-1-(4-fluorophenyl)-2-methyl-1H—imidazo[4,5-c]quinoline (295-297) |
| 111 | 88 | 4-chloro-1-(4-methoxyphenyl)-2-methyl-1H—imidazo[4,5-c]quinoline (211-213) |
| 112 | 89 | 4-chloro-1-(4-fluorophenyl)-1H—imidazo-[4,5-c]quinoline (248-250) |
| 113 | 130, Part D | 4-chloro-1-[2-(phenyl)ethyl]-1H—imidazo-[4,5-c]quinoline (176-188) |
| 114 | 92 | 4-chloro-1-methyl-1H—imidazo[4,5-c]-quinoline (179-181) |
| 115 | 166, Part B | 1-benzyl-4-chloro-2-methyl-1H—imidazo[4,5-c]quinoline (216-218) |
| 116 | 94 | 4-chloro-1-isobutyl-2-methyl-1H—imidazo[4,5-c]quinoline (152-155) |
| 117 | 95 | 4-chloro-1,2-dimethyl-8-fluoro-1H—imidazo-[4,5-c]quinoline (not taken) |

EXAMPLE 118

To a stirred, cold (5° C.) mixture of 29.1 g (0.136 mole of 1-(2-hydroxyethyl)-1H-imidazo[4,5-c]quinoline (from Example 52) and 500 ml of pyridine was added, in small portions, 23.9 g (0.17 mole) of benzoyl chloride. The mixture was permitted to warm to about 20° C. slowly, and was then stirred for eighteen hours at 20° C. The solution was evaporated, and water was added to the residue. The solid was separated by filtration, washed with water and recrystallized from a 50:50 ethyl acetate/hexane mixture. Recrystallization from ethyl acetate and again from ethanol provided white crystals of 1-(2-benzoyloxyethyl)-1H-imidazo[4,5-c]quinoline, m.p. 149°-151° C. Analysis: Calculated for $C_{19}H_{15}N_3O_2$: %C, 71.9; %H, 4.8; %N, 13.2; Found: %C, 71.8; %H, 4.6; %N, 13.2.

EXAMPLE 119

A mixture of 67.5 g (0.213 mole) of 1-(2-benzoyloxyethyl)-1H-imidazo[4,5-c]quinoline (from Example 118), 36.3 g (0.32 mole) of 30% hydrogen peroxide and 450 ml of glacial acetic acid was heated at 65° C. for two days with stirring. The solution was then evaporated in vacuo, and the residue was added to water. The mixture was neutralized with aqueous sodium hydroxide solution and sodium bicarbonate. The solid was separated by filtration, washed with water and recrystallized from methanol to provide tan solid 1-(2-benzoyloxyethyl)-1H-imidazo[4,5-c]-quinolin-5-oxide.

EXAMPLE 120

A mixture of 50 g (0.15 mole) of 1-(2-benzoyloxyethyl)-1H-imidazo[4,5-c]quinolin-5-oxide (from Example 119) and 200 ml of phosphorus oxychloride was heated for two hours on a steam bath. The mixture was then partially evaporated in vacuo. The mixture was then poured over ice and the solution was neutralized with sodium hydroxide. The product was separated by filtration, dissolved in dichloromethane, and the solution was washed with aqueous sodium bicarbonate solution and then dried. Evaporation provided a solid which was recrystallized from a 50:50 methanol:dichloromethane solution to provide white 1-(2-benzoyloxyethyl)-4-chloro-1H-imidazo[4,5-c]quinoline, m.p. 186°-190° C. Analysis: Calculated for $C_{19}H_{14}ClN_3O_2$: %C, 64.9; %H, 4.0; %N, 12.0; Found: %C, 64.8; %H, 3.8; %N, 12.1.

EXAMPLE 121

A mixture of 25.3 g (0.072 mole) of 1-(2-benzoyloxyethyl)-4-chloro-1H-imidazo[4,5-c]quinoline (from Example 120) and 500 ml of 10% ammonia in methanol was stirred at about 20° C. for three days, and was filtered and then evaporated to low volume. The slurry was mixed with diethyl ether, and the solid was separated by filtration, washed with ether and recrystallized from methanol to provide white crystals of 4-chloro-1-(2-hydroxyethyl)-1H-imidazo[4,5-c]quinoline, m.p. 185°-187° C. Analysis: Calculated for $C_{12}H_{10}ClN_3O$: %C, 58.2; %H, 4.1; %N, 17.0; Found: %C, 58.0; %H, 4.0; %N, 17.3.

EXAMPLE 122

To a solution of 3.0 g (0.013 mole) of 1-isobutyl-1H-imidazo[4,5-c]quinoline (from Example 50) in 150 ml of ethanol was added hydrogen chloride gas. After stirring for about one hour the solid 1-isobutyl-1H-imidazo[4,5- c]quinoline hydrochloride hydrate was separated by filtration and recrystallized from ethanol to provide off-white crystals, m.p. 227°–229° C. Analysis: Calculated for $C_{14}H_{15}N_3 \cdot HCl \cdot H_2O$: %C, 60.1: %H, 6.5; %H, 15.0; Found: %C, 60.2; %H, 6.2; %N, 15.4.

EXAMPLE 123

Part A

Using the method of Example 118, benzoyl chloride was reacted with 1-(2,3-dihydroxypropyl)-1H-imidazo[4,5-c]quinoline (from Example 70) to provide 1-(2,3-dibenzoyloxypropyl)-1H-imidazo[4,5-c]quinoline.

Part B

The crude product from Part A was reacted with hydrogen peroxide according to the method of Example 119 to provide 1-(2,3-dibenzoyloxypropyl)-1H-imidazo[4,5-c]-quinolin-5-oxide as a pale yellow solid, the melting point of crude material being 73°–82° C.

Part C

The product from Part B was reacted with phosphorous oxychloride according to the method of Example 120 to provide 4-chloro-1-(2,3-dibenzoyloxypropyl)-1H-imidazo[4,5-c]quinoline, m.p. 162°–165° C. after recrystallization from ethanol. Analysis: Calculated for $C_{27}H_{20}ClN_3O_4$: %C, 66.7; %H, 4.1; %N, 8.6; Found: %C, 66.3; %H, 3.9; %N, 8.4.

Part D

Hydrolysis of the product from Part C according to the method of Example 121 provides 4-chloro-1-(2,3-dihydroxypropyl)-1H-imidazo[4,5-c]quinoline.

EXAMPLE 124

Part A 1-(2,3-Dihydroxypropyl)-1H-imidazo[4,5-c]quinoline (from Example 70) was reacted with excess acetic anydride to provide 1-(2,3-diacetoxypropyl)-1H-imidazo[4,5-c]quinoline.

Part B

The product of Part A was reacted with hydrogen peroxide according to the method of Example 119 to provide 1-(2,3-diacetoxypropyl)-1H-imidazo[4,5-c]quinoline-5-oxide as a brownish-yellow solid, the melting point of the crude material being 84°–96° C.

Part C

The product of Part B was reacted with phosphorus oxychloride according to the method of Example 120 to provide 4-chloro-1-(2,3-diacetoxypropyl)-1H-imidazo[4,5-c]-quinoline.

Part D

The product of Part C was hydrolyzed according to the method of Example 121 to provide 4-chloro-1-(2,3-dihydroxypropyl)-1H-imidazo[4,5-c]quinoline. Recrystallization from ethanol provided product, m.p. 223°–225° C. Analysis: Calculated for $C_{13}H_{12}ClN_3O_2$: %C, 56.2, %H, 4.4; %N, 15.1; Found: %C, 55.8, %H, 4.3; %N, 15.1.

EXAMPLE 125

To a stirred solution of 4.0 g (0.0117 mole) of 1-(2,3-diacetoxypropyl)-1H-imidazo[4,5-c]quinolin-5-oxide (from Example 124, Part B) in 50 ml of methanol was added about 12 drops of 25% sodium methoxide solution. After one hour the product was collected by filtration, washed with methanol and recrystallized from ethanol to provide 1-(2,3-dihydroxypropyl)-1H-imidazo[4,5-c]quinolin-5-oxide, m.p. 240°–242° C. Analysis: Calculated for $C_{13}H_{13}N_3O_3$: %C, 60.2; %H, 5.1; %N, 16.2; Found: %C, 60.0; %H, 5.0; %N, 15.8.

EXAMPLE 126

Excess acetic anhydride (100 ml) was refluxed for 0.5 hour with 1-(2,3-dihydroxypropyl)-2-methyl-1H-imidazo[4,5-c]quinoline (from Example 53) to provide 1-(2,3-diacetoxypropyl)-2-methyl-1H-imidazo[4,5-c]quinoline. This product was reacted with hydrogen peroxide using the method of Example 119 to provide 1-(2,3-diacetoxypropyl)-2-methyl-1H-imidazo[4,5-c]quinolin-5-oxide as a yellow solid. This crude product was reacted with phosphorous oxychloride according to the method of Example 120 to provide the product 4-chloro-(2,3-diacetoxypropyl)-2-methyl-1H-imidazo[4,5-c]quinoline. This product was dissolved in methanol saturated with ammonia, and the solution was stirred for three days. The product obtained was 4-chloro-1-(2,3-dihydroxypropyl)-2-methyl-1H-imidazo[4,5-c]quinoline.

EXAMPLE 127

Part A

Using the method of Example 1, benzylamine and 4-chloro-3-nitroquinoline were reacted to provide 4-benzylamino-3-nitroquinoline. The structural assignment for the crude product (m.p. 178°–196° C.) was supported by infrared spectral analysis.

Part B

Using the method of Example 26, 42.2 g (0.15 mole) of 4-benzylamino-3-nitroquinoline was reduced to provide 3-amino-4-(benzylamino)quinoline as a tan solid.

Part C

To the product from Part B was added 48.7 g (0.5 mole) of diethoxymethyl acetate and the mixture was heated on a steam bath for one hour, and was then maintained at reflux for 0.5 hour. The solution was added to a stirred excess of concentrated ammonium hydroxide. The solid was separated by filtration and washed sequentially with water, 10:1 diethyl ether:ethanol and 1:1 hexane:diethyl ether. Recrystallization from isopropanol provided pale yellow needles of 1-benzyl-1H-imidazo[4,5-c]quinoline, m.p. 179°–181° C. Analysis: Calculated for $C_{17}H_{13}N_3$: %C, 78.7; %H, 5.1: %N, 16.2; Found: %C, 78.6; %H, 4.8; %N, 16.3.

EXAMPLE 128

Part A

A mixture of 26.1 g (0.125 mole) of 4-chloro-3-nitroquinoline, 16.4 g (0.1275 mole) of 95% cyclohexylmethylamine and 16.5 g (0.125 mole) of 95% diisopropyl ethylamine in 300 ml of tetrahydrofuran was heated on a steam bath for 0.5 hour. The solution was evaporated and the residue was slurried in methanol, filtered and washed with methanol. Recrystallization from methanol provided yellow platelets of 4-cyclohexylmethylamino-3-nitroquinoline, m.p. 140°–142° C. Analysis: Calculated for $C_{16}H_{19}N_3O_2$: %C, 67.3; %H, 6.7; %N, 14.7; Found: %C, 67.3; %H, 6.6; %N, 14.7.

Part B

Using the method of Example 26, 17 g (0.60 mole) of 4-cyclohexylmethylamino-3-nitroquinoline was reduced to provide 3-amino-4-cyclohexylmethylaminoquinoline.

Part C

The crude product from Part B was heated at reflux for 2.5 hours in 250 ml of 98% formic acid to provide 1-cyclohexylmethyl-1H-imidazo[4,5-c]quinoline as a pale yellow solid.

EXAMPLE 129

Using the method of Example 1, 4-chloro-3-nitroquinoline was reacted with 4-chlorobenzylamine to provide yellow solid 4-(4-chlorobenzylamino)-3-nitroquinoline, melting point of crude product 168°-173° C.

EXAMPLE 130

Part A

Using the method of Example 1, 4-chloro-3-nitroquinoline was reacted with 2-(phenyl)ethylamine to provide yellow solid 3-nitro-4-[2-(phenyl)ethylamino]quinoline, the melting point of the crude product being 174°-180° C.

Part B

Using the method of Example 26, 3-nitro-4-[2-(phenyl)ethylamino]quinoline from Part A was reduced to provide 3-amino-4-[2-(phenyl)ethylamino]quinoline.

Part C

Using the method of Example 49, 3-amino-4-[2(phenyl)ethylamino]quinoline was reacted with triethyl orthoformate and formic acid to provide 1-[2-(phenyl)ethyl]-1H-imidazo[4,5-c]quinoline, m.p. 105°-108° C.

Part D

Using the method of Example 74, 1-[2-(phenyl)ethylamino]-1H-imidazo[4,5-c]quinoline was converted to yellow solid 1-[2-(phenyl)ethyl]-1H-imidazo[4,5-c]quinolin-5-oxide, melting point of crude product, 73°-95° C.

EXAMPLE 131

To a solution of 4.0 g (0.0155 mole) of 1-isobutyl-2-mercapto-1H-imidazo[4,5-c]quinoline (from Example 164, Part B) in 40 ml of methanol was added 3.7 g of 25% sodium methoxide in methanol, followed by the addition of 2.4 g (0.0171 mole) of methyl iodide. The solution was heated on a steam bath for 0.5 hour, and was then evaporated. Water was added to the residue and the mixture was extracted with dichloromethane. The extracts were washed with water, dried over sodium chloride and evaporated. The residue was dissolved in diethyl ether and the mixture was saturated with hydrogen chloride. The precipitate was separated by filtration, washed with ether, and recrystallized from a mixture of ethanol and ether to provide 1-isobutyl-2-methylthio-1H-imidazo[4,5-c]quinoline hydrochloride, m.p. 214°-216° C. Analysis: Calculated for $C_{15}H_{17}N_3S \cdot HCl$: %C, 58.5; %H, 5.9; %N, 13.7; Found: %C, 57.9; %H, 5.7; %N, 13.7.

EXAMPLE 132

A sample of 2-(3-aminopropyl)-1,8-dimethyl-1H-imidazo[4,5-c]quinoline dihydrochloride (from Example 147) was dissolved in water. Excess sodium hydroxide was added to neutralize the hydrochloric acid and then excess acetic anhydride was added. The precipitate was separated by filtration, washed with water, and recrystallized from water to provide 2-(3-acetamidopropyl)-1,8-dimethyl-1H-imidazo[4,5-c]quinoline, m.p. 213°-215° C. Analysis: Calculated for $C_{17}H_{20}N_4O$: %C, 68.9; %H, 6.8; %N, 18.9; Found: %C, 68.8; %H, 6.8; %N, 19.0.

EXAMPLE 133

A mixture of 2.7 g (0.0080 mole) of 1-(2,3-diacetoxypropyl)-1H-imidazo[4,5-c]quinolin-5-oxide (from Example 124, Part B) and 50 ml of acetic anhydride was heated at its reflux temperature for one hour. The solution was evaporated and the residue was mixed with 65 ml of methanol. The mixture was basified (to pH 9–10) with 25% sodium methoxide in methanol. The precipitate was separated by filtration, washed with methanol and recrystallized twice from methanol. The product was 1-(2,3-dihydroxypropyl)-4-hydroxy-1H-imidazo[4,5-c]quinoline hydrate, m.p. 214°-217° C. Analysis: Calculated for $C_{13}H_{13}N_3O_3$: 0.50H$_2$O: %C, 58.2; %H, 5.3; %N, 15.7; Found: %C, 57.7; %H, 4.9; %N, 15.5.

EXAMPLE 134

Using the method of Example 133, 1,2-dimethyl-1H-imidazo[4,5-c]quinolin-5-oxide (from Example 91) was reacted with acetic anhydride to provide 1,2-dimethyl-4-hydroxy-1H-imidazo[4,5-c]quinoline, m.p. >300° C. Analysis: Calculated for $C_{12}H_{11}N_3O$: %C, 67.7; H, 5.2; %N, 19.7; Found: %C, 67.1; %H, 5.1; %N, 19.5.

EXAMPLE 135

Using the method of Example 133, 1-(4-methoxyphenyl)-1H-imidazo[4,5-c]quinolin-5-oxide (from Exmaple 86) was reacted with acetic anhydride to provide 4-hydroxy-1-(4-methoxyphenyl)-1H-imidazo[4,5-c]quinoline m.p. >300° C. after recrystallization from N,N-dimethylformamide. Analysis: Calculated for $C_{17}H_{13}N_3O_2$: %C, 70.1; %H, 4.5; %N, 14.4; Found: %C, 70.0; %H, 4.4; %N, 14.5.

EXAMPLE 136

Using the method of Example 133, 1-(2-hydroxyethyl)-1H-imidazo[4,5-c]quinolin-5-oxide prepared by hydrolysis of the compound of Example 120 was reacted with acetic anhydride to provide 4-hydroxy-1-(2-hydroxyethyl)-1H-imidazo[4,5-c]quinoline.

The compound 4-hydroxy-1-(2-hydroxyethyl)-1H-[4,5-c]quinoline was found to have m.p. >300° C. after recrystallization from N,N-dimethylformamide. Analysis: Calculated for $C_{12}H_{11}N_3O_2$: %C, 62.9; %H, 4.8; %N, 18.7; Found: %C, 62.7; %H, 4.7; %N, 18.3.

EXAMPLE 137

A mixture of 2.2 g (0.0115) of 3,4-diamino-6-fluoro-2-methylquinoline (from Example 43) and 50 ml of 95% formic acid was heated at its reflux temperature for two hours, and was then evaporated. Water (100 ml) was added to the residue, and the mixture was basified with 50% aqueous sodium hydroxide solution to pH 9 to 10. The precipitate formed was separated by filtration and washed with water. Recrystallization from ethanol provided white solid 8-fluoro-4-methyl-1H-imidazo[4,5-c]quinoline hydrate, m.p. >250° C. Analysis: Calculated for $C_{11}H_8FN_3.H_2O$: %C, 60.3; %H, 4.6; %N, 19.2; Found: %C, 60.1; %H, 4.7; %N, 18.5.

EXAMPLE 138

Using the method of Example 137, 3-amino-4-(2,3-dihydroxypropylamino)-6-fluoro-2-methylquinoline (from Example 42) was reacted with formic acid to provide 1-(2,3-dihydroxypropyl)-8-fluoro-4-methyl-1H-imidazo[4,5-c]quinoline hydrate, m.p. 237°-239° C. Analysis: Calculated for $C_{14}H_{14}FN_3O_2.H_2O$: %C, 57.3; %H, 5.5; %N, 14.3; Found: %C, 57.6; %H, 5.4; %N, 14.4.

EXAMPLE 139

Using the method of Example 138, 3-amino-4-benzylamino-6-fluoro-2-methylquinoline (from Example 45) was reacted with formic acid to provide 1-benzyl-8-fluoro-4-methyl-1H-imidazo[4,5-c]quinoline hydrate, m.p. 178°-181° C. Analysis: Calculated for $C_{18}H_{14}FN_3.0.25H_2O$: %C, 73.1; %H, 4.9; %N, 14.2; Found: %C, 73.0; %H, 4.7; %N, 14.3.

EXAMPLE 140

Using the method of Example 137, 3-amino-6-fluoro-2-methyl-4-methylaminoquinoline (from example 44) was reacted with formic acid to provide 1,4-dimethyl-8-fluoro-1H-imidazo[4,5-c]quinoline, m.p. 184°-186° C. Analysis: Calculated for $C_{12}H_{10}FN_3$: %C, 67.0; %H, 4.7; %N, 19.5; Found: %C, 66.6; %H, 4.4; %N, 19.7.

EXAMPLE 141

Using the method of Example 137, 3-amino-4-[2-(N,N-dimethylamino)ethylamino]quinoline (from Example 46) was reacted with formic acid to provide 1-[2-(N,N-dimethylamino)ethyl]-1H-imidazo[4,5-c]quinoline. The product was dissolved in ethanol and hydrogen chloride was bubbled into the solution. The precipitate was separated by filtration, washed with ethanol and recrystallized from ethanol. The product was 1-[2-(N,N-dimethylamino)ethyl]-1H-imidazo[4,5-c]quinoline trihydrochloride hydrate, m.p. >250° C. Analysis: Calculated for $C_{14}H_{16}N_4.3HCl.H_2O$: %C, 45.8; %H, 5.5; %N, 15.3: Found: %C, 46.0; %H, 5.2; %N, 15.5.

EXAMPLE 142

Using the method of Example 1, 4-chloro-3-nitroquinoline was reacted with 4-aminophenylacetic acid in N,N-dimethylformamide in the presence of triethylamine to provide N-(3-nitro-4-quinolinyl)-4-aminophenylacetic acid. This acid was reduced using the method of Example 26 to provide N-(3-amino-4-quinolinyl)-4-aminophenylacetic acid. This diamine was then reacted with formic acid using the method of Example 137 to provide 1-(4-carboxymethylphenyl)-1H-imidazo[4,5-c]quinoline. Recrystallization from methanol provided solid of m.p. 236°-240° C. Analysis: Calculated for $C_{18}H_{13}N_3O_2$: %C, 71.3; %H, 4.3; %N, 13.9; Found; %C, 70.8; %H, 4.3; %N, 13.7.

EXAMPLE 143

A mixture of 4.5 g (0.020 mole) of 3-amino-6-methyl-4-(methylamino)quinoline hydrochloride (from Example 32), 3.8 g (0.050 mole) of glycolic acid and 75 ml of 4 N hydrochloric acid was heated at its reflux temperature for two hours. The solution was cooled, and 50% aqueous sodium hydroxide was then added to make the solution slightly basic. The precipitate was separated by filtration and washed with water. The solid was redissolved in dilute hydrochloric acid and reprecipitated with ammonium hydroxide to provide 1,8-dimethyl-2-hydroxymethyl-1H-imidazo[4,5-c]quinoline hydrochloride hydrate. Analysis: Calculated for $C_{13}H_{13}N_3O.HCl.H_2O$: %C, 55.4; %H, 5.7; %N, 14.9; Found: %C, 55.2; %H, 5.6; %N, 15.5.

EXAMPLE 144

A mixture of 4.5 g (0.0201 mole) of 3-amino-6-methyl-4-(methylamino)quinoline hydrochloride (from Example 32), 9.1 g (0.080 mole) of trifluoroacetic acid and 100 ml of 4 N hydrochloric acid was heated at its reflux temperature for three hours. The solution was cooled and basified with ammonium hydroxide. The precipitate was separated by filtration and washed with water. Recrystallization from isopropanol provided 1,8-dimethyl-2-trifluoromethyl-1H-imidazo[4,5-c]quinoline, m.p. 220°-223° C. Analysis: Calculated for $C_{13}H_{10}F_3N_3$: %C, 58.9; %H, 3.8; %N, 15.8; Found: %C, 58.6; %H, 3.7; %N, 16.2.

EXAMPLE 145

Using the method of Example 144, 3,4-diaminoquinoline (from Example 39) was reacted with trifluoroacetic acid to provide 2-trifluoromethyl-1H-imidazo[4,5-c]quinoline, m.p. 252°-254° C. Analysis: Calculated for $C_{11}H_6F_3N_3$: %C, 55.7; %H, 2.5; %N, 17.7; Found: %C, 55.3; %H, 2.3; %N, 18.2.

EXAMPLE 146

To a solution of 6.6 g (0.041 mole) of 3,4-diaminoquinoline (from Example 39), 2.0 ml of glacial acetic acid, 35 cc of ethanol and 35 ml of water was added 9.3 g (0.045 mole) of N-carbomethoxy-S-methylisothiourea, and the mixture was heated at its reflux temperature for two hours. Evaporation provided a residue which was suspended in ethanol, separated by filtration and washed with water. Recrystallization from ethanol provided methyl 1H-imidazo[4,5-c]quinolin-2-carbamate hydrate, m.p. >250° C. Analysis: Calculated for $C_{12}H_{10}N_4O_2.0.75H_2O$: %C, 56.4; %H, 4.5; %N, 21.9; Found: %C, 56.1; %H, 4.4; %N, 22.4.

EXAMPLE 147

A mixture of 5.8 g (0.026 mole) of 3-amino-6-methyl-4-(methylamino)quinoline (the hydrochloride salt of which having been obtained in Example 32), 4.1 g (0.040 mole) of 4-aminobutyric acid and 100 ml of 4 N hydrochloric acid was heated at its reflux temperature for about 65 hours. The solution was cooled and diluted to 500 ml total volume with isopropanol. The precipitate was separated by filtration, and then recrystallized from aqueous isopropanol to provide yellow crystals of 2-(3-aminopropyl)-1,8-dimethyl-1H-imidazo[4,5-c]quinoline dihydrochloride, m.p. >300° C. Analysis: Calculated for $C_{15}H_{18}N_4.2HCl$: %C, 55.0; %H, 6.2; %N, 17.1; Found: %C, 54.3; %H, 6.2: %N, 17.1.

EXAMPLE 148

Using the method of Example 147, 3,4-diaminoquinoline (from Example 39) was reacted with triethyl orthoacetate to provide 2-methyl-1H-imidazo[4,5-c]quinoline as a tan solid, m.p. 242°-245° C.

EXAMPLE 149

Using the method of Example 147, 3-amino-4(methylamino)quinoline (the hydrochloride salt of which having been obtained in Exmple 27) was reacted with isobutyric acid to provide 2-isopropyl-1-methyl-1H-imidazo[4,5-c]quinoline. The crude product was dissolved in ethyl acetate and an excess of concentrated hydrochloric acid was added. The precipitate was separated by filtration and recrystallized from ethanol to provide 2-isopropyl-1-methyl-1H-imidazo[4,5-c]quinoline hydrochloride, m.p. 260°–263° C. This salt was suspended in water and the mixture was basified (pH 8–10) with 50% aqueous sodium hydroxide. The solid was separated by filtration, washed with water and recrystallized from hexane to provide the free base as the hydrate, m.p. 76°–81° C. Analysis: Calculated for $C_{14}H_{15}N_3.0.25H_2O$: %C, 73.2; %H, 6.8; %N, 18.3; Found: %C, 73.0 %H, 7.0; %N, 18.4.

EXAMPLE 150

Using the method of Example 74, 1,4-dimethyl-8-fluoro-1H-imidazo[4,5-c]quinoline (from Example 140) was reacted with hydrogen peroxide to provide 1,4-dimethyl-8-fluoro-1H-imidazo[4,5-c]quinolin-5-oxide, m.p. 245°–248° C. Analysis: Calculated for $C_{12}H_{10}FN_3O$: %C, 62.3; %H, 4.4; %N, 18.2; Found: %C, 62.7; %H, 4.3; %N, 18.3.

EXAMPLE 151

A mixture of 2.0 g (0.0068 mole) of 1-benzyl-4-chloro-1H-imidazo[4,5-c]quinoline (from Example 99) and 25 ml of morpholine was heated at its reflux temperature for one hour. The solution was evaporated, and 30 ml of water was added to the residue. The solid which did not dissolve was separated by filtration, washed with water and recrystallized from ethanol. The product obtained was 1-benzyl-4-(4-morpholino)-1H-imidazo[4,5-c]quinoline hydrate, m.p. 160°–162° C. Analysis: Calculated for $C_{21}H_{20}N_4O.0.25H_2O$: %C, 72.3; %H, 5.9; %N, 16.1; Found: %C, 72.1; %H, 5.8; %N, 16.0.

Using the general method exemplified in Example 151, and starting with morpholine and the indicated intermediate of Formula IX, compounds of the invention of Formula X shown in Table VI were prepared.

TABLE VI

| Ex. No. | Intermediate of Formula IX (Example No.) | Product of Formula X (melting point in °C.) |
|---|---|---|
| 152 | 114 | 1-methyl-4-(4-morpholino)-1H—imidazo-[4,5-c]quinoline (207–209) |
| 153 | 102 | 1,8-dimethyl-4-(4-morpholino)-1H—imidazo[4,5-c]quinoline (250–256) |

EXAMPLE 154

A mixture of 40% aqueous methylamine (25 ml) and 5.0 g (0.023 mole) of 4-chloro-1-methyl-1H-imidazo[4,5-c]quinoline (from Example 114) was placed in a metal pressure reactor and heated at 112° C. for about 16 hours. After cooling, the solid was separated by filtration, washed with water, dried and recrystallized from ethanol to provide N,1-dimethyl-1H-imidazo[4,5-c]quinolin-4-amine, m.p. 216°–218° C. Analysis: Calculated for $C_{12}H_{12}N_4$: %C, 67.9; %H, 5.7; %N, 26.4; Found: %C, 67.9; %H, 5.6; %N, 26.4.

Using the method of Example 154, the following compounds of Examples 154 and 156 were prepared:

EXAMPLE 155

N,N,-1-trimethyl-1H-imidazo[4,5-c]quinolin-4-amine (m.p. 162°–164° C.).

EXAMPLE 156

1-(2,3-dihydroxypropyl)-N-methyl-1H-imidazo[4,5-c]-quinolin-4-amine (m.p. 201°–203° C.).

EXAMPLE 157

A mixture of 3.6 g (0.0116 mole) of 4-chloro-1-(4-methoxyphenyl)-1H-imidazo[4,5-c]quinoline (from Example 109), 25.1 g (0.116 mole) of 25% sodium methoxide in methanol and 50 ml of methanol was heated its reflux temperature for one hour. Evaporation provided a residue which was diluted with 75 ml of water. The precipitate was separated by filtration, washed with water and recrystallized from ethanol to provide 4-methoxy-1-(4-methoxyphenyl)-1H-imidazo[4,5-c]quinoline, m.p. 180°–182° C. Analysis: Calculated for $C_{18}H_{15}N_3O_2$: %C, 70.8; %H, 5.0; %N, 13.8; Found: %C, 70.6; %H, 5.0; %N, 13.9.

EXAMPLE 158

Using the method of Example 157, 4-chloro-1-methyl-1H-imidazo[4,5-c]quinoline (from Example 114) was reacted with sodium methoxide to provide 4-methoxy-1-methyl-1H-imidazo[4,5-c]quinoline, melting point after recrystallization from ethyl acetate 160°–162° C. Analysis: Calculated for $C_{12}H_{11}N_3O$: %C, 67.6; %H, 5.2; N, 19.7; Found: %C, 67.3; %H, 5.0; %N, 19.8.

EXAMPLE 159

Using the method of Example 157, 4-chloro-1-(2,3-dihydroxypropyl)-1H-imidazo[4,5-c]quinoline (from Example 124, Part D) was reacted with sodium methoxide to provide 1-(2,3-dihydroxypropyl)-4-methoxy-1H-imidazo[4,5-c]quinoline, m.p. 214°–216° C. after recrystallization from isopropanol. Analysis: Calculated for $C_{14}H_{15}N_3O_3$: %C, 61.5; %H, 5.5; N, 15.4; Found: %C, 61.3; %H, 5.5; %N, 15.4.

EXAMPLE 160

To a mixture of 24.75 g (0.1145 mole) of 25% sodium methoxide in methanol and 100 ml of ethanol was added 8.5 g (0.1374 mole) of ethanethiol, followed by the addition of 5.0 g (0.0229 mole) of 4-chloro-1-methyl-1H-imidazo[4,5-c]quinoline (from Example 114). The mixture was heated at its reflux temperature for one hour, and was then evaporated. Water was added to the residue and the solid obtained was separated by filtration and washed with water. Recrystallization from ethyl acetate provided yellow crystals of 4-ethylthio-1-methyl-1H-imidazo[4,5-c]quinoline, m.p. 112°–115° C. Analysis: Calculated for $C_{13}H_{13}N_3S$: %C, 64.2; %H, 5.4; %N, 17.3; Found: %C, 64.4; H, 5.3; %N, 17.6.

EXAMPLE 161

Using the general procedure of Example 160, and substituting thiophenol for ethanethiol, 4-chloro-1-methyl-1H-imidazo[4,5-c]quinoline (from Example 114) was converted to 1-methyl-4-phenylthio-1H-imidazo[4,5-c]quinoline, m.p. 213°–215° C. after recrystallization from ethyl acetate. Analysis: Calculated for $C_{17}H_{13}N_3S$: %C, 70.1; %H, 4.5; %N, 14.4; Found; %C, 69.8; %H, 4.3; %N, 14.7.

EXAMPLE 162

To a solution of 4.4 g (0.071 mole) of 1-isobutyl-2-mercapto-1H-imidazo[4,5-c]quinoline (from Example 164, Part B below) in 45 ml of methanol and was added 4.1 g (0.0188) of 25% sodium methoxide in methanol, then 2.4 g (0.0188 mole) of benzyl chloride. The solution was heated at reflux for 0.5 hour, then evaporated. Water was added to the residue, and the mixture was extracted with dichloromethane. The extracts were dried over sodium chloride, and then evaporated. The residue was dissolved in diethyl ether, and the solution was saturated with hydrogen chloride. The precipitate was separated by filtration, washed with ether and recrystallized from a mixture of ethanol and diethyl ether to provide 2-benzylthio-1-isobutyl-1H-imidazo[4,5-c]quinoline hydrochloride, m.p. 205°–207° C. Analysis: Calculated for $C_{21}H_{21}N_3S.HCl$: %C, 65.7; %H, 5.8; %N, 10.9; Found: %C, 65.4; %H, 5.6; %N, 10.9.

EXAMPLE 163

Using the method of Example 162, 2-mercapto-1-methyl-1H-imidazo[4,5-c]quinoline (from Example 165 below) was reacted with benzyl chloride to provide 2-benzylthio-1-methyl-1H-imidazo[4,5-c]quinoline. Recrystallization first from isopropanol then from ethanol provided solid product, m.p. 160°–163° C. Analysis: Calculated for $C_{18}H_{15}N_3S$: %C, 70.8; %H, 5.0; %N, 13.8. Found: %C, 70.3; %H, 4.7; %N, 13.7.

EXAMPLE 164

Part A

To a solution of 15.0 g (0.0612 mole) of 4-isobutylamino-3-nitroquinoline (from Example 1) in ethanol was added about 0.5 g of 5% platinum on charcoal, and the mixture was hydrogenated on a Parr apparatus at about 20° C. The mixture was filtered to provide a solution of 3-amino-4-(isobutylamino)quinoline.

Part B

To the solution from Part A was added first 10 ml of carbon disulfide, and then 4.6 g (0.07 mole) of 85% potassium hydroxide. The solution was heated on a steam bath for two hours, and was evaporated to near dryness. The residue was dissolved in water, the solution acidified to pH 5 to 6 with glacial acetic acid and the precipitate separated by filtration and washed with water. Recrystallization from ethanol provided yellow 1-isobutyl-2-mercapto-1H-imidazo[4,5-c]quinoline, m.p. >300° C. Analysis: Calculated for $C_{14}H_{15}N_3S$: %C, 65.3; %H, 5.9; %N, 16.3; Found: %C, 64.8; %H, 5.7; %N, 16.3.

EXAMPLE 165

Using the method of Example 164, 4-methylamino-3-nitroquinoline (from Example 2) was converted to 2-mercapto-1-methyl-1H-imidazo[4,5-c]quinoline.

EXAMPLE 166

Part A

Using the method of Example 49, 3-amino-4-(benzylamino)quinoline (from Example 127, Part B), was reacted with triethyl orthoacetate and acetic acid to provide 1-benzyl-2-methyl-1H-imidazo[4,5-c]quinoline hydrate, m.p. 145°–147° C. Analysis: Calculated for $C_{18}H_{15}N_3.2.25H_2O$: %C, 68.9; %H, 6.3, %N, 13.4; Found: %C, 69.2; %H, 6.0; %N 13.4.

Part B

Using the method of Example 74, 1-benzyl-2-methyl-1H-imidazo[4,5-c]quinoline was converted to 1-benzyl-2-methyl-1H-imidazo[4,5-c]quinolin-5-oxide hydrate, m.p. 193°–196° C. Analysis: Calculated for $C_{18}H_{13}N_3O..2.25H_2O$: %C, 65.6; %H, 6.0; %N, 12.7; Found: %C, 65.4; %H, 5.7; %N, 12.5.

EXAMPLE 167

To a solution of 5.7 g (0.30 mole) of 4-hydroxy-3-nitroquinoline in 50 ml of N,N-dimethylformamide was added 9.3 g (0.60 mole) of phosphorus oxychloride. The solution was heated on a steam bath for 5 minutes, then poured with stirring into 200 ml of 40% aqueous methylamine. The mixture was heated on a steam bath for fifteen minutes, then diluted with 200 ml of water. The solid was separated by filtration, then dissolved in dilute hydrochloric acid. The solution was filtered and the filtrate was basified with ammonium hydroxide. The solid precipitate was separated by filtration, washed with water and dried to provide Yellow solid 4-methylamino-3-nitroquinoline, m.p. 167°–171° C.

EXAMPLE 168

To a solution of 4.8 g (0.0311 mole) of phosphorus oxychloride in 20 ml of N,N-dimethylformamide was added, in small portions, 5.0 g (0.207 mole) of 1-isobutyl-1H-imidazo[4,5-c]quinoline-5-oxide. The solution was stirred for 15 minutes at 20° C., then heated on a steam bath for 15 minutes. The solution was cooled to 20° C., then poured into stirred ice. The solution was basified to pH 8 with concentrated ammonium hydroxide. The yellow solid precipitate was separated by filtration, washed sequentially with water and diethyl ether, and dried to provide 4-chloro-1-isobutyl-1H-imidazo[4,5-c]quinoline hydrate, m.p. 103°–107° C. Recrystallization twice from ethyl acetate with drying provided 4-chloro-1-isobutyl-1H-imidazo[4,5-c]quinoline, m.p. 135°–137° C. Analysis: Calculated for $C_{14}H_{14}ClN_3$: %C, 64.7; %H, 5.4; %N, 16.2; Found: %C, 64.6; %H, 5.5; %N, 16.1.

EXAMPLE 169

Using the method of Example 49, 3-amino-4-[2-(phenyl)ethylamino]quinoline (from Example 130, Part B) was reacted with triethyl orthoacetate and acetic acid to provide 2-methyl-1-[2-(phenyl)ethyl]-1H-imidazo[4,5-c]-quinoline.

EXAMPLE 170

Using the method of Example 157, 4-chloro-1-isobutyl-1H-imidazo[4,5-c]quinoline (from Example 96) was reacted with sodium methoxide to provide 1-isobutyl-4-methoxy-1H-imidazo[4,5-c]quinoline, melting point 111°–114° C. after sequential recrystallizations from aqueous ethanol and diethyl ether. Analysis: Calculated for $C_{15}H_{17}N_3O$: %C, 70.6; %H, 6.7; %N, 16.5; Found: %C, 70.6; %H, 6.7; %N, 16.5.

EXAMPLE 171

Using the method of Example 133, 1-isobutyl-1H-imidazo[4,5-c]quinolin-5-oxide (from Example 74) was reacted with acetic anhydride to provide 4-hydroxy-1-isobutyl-1H-imidazo[4,5-c]quinoline, m.p. >300° C. after recrystallization from N,N-dimethylformamide. Analysis: Calculated for $C_{14}H_{15}N_3O$: %C, 69.7; %H, 6.3; %N, 17.4; Found: %C, 69.8; %H, 6.4: %N, 17.6.

EXAMPLE 172

Part A

Using the method of Example 26, 4-(4-chlorobenzylamino)-3-nitroquinoline (from Example 23) was reduced to provide 3-amino-4-(4-chlorobenzylamino)quinoline.

Part B

The product from Part A was reacted with triethyl orthoacetate and acetic acid using the method of Example 49 to provide 1-(4-chlorobenzyl)-2-methyl-1H-imidazo[4,5-c]quinoline, m.p. 183°–185° C.

EXAMPLE 173

Using the general method exemplified in Example 151, 4-chloro-1-methyl-1H-imidazo[4,5-c]quinoline (from Example 114) was reacted with n-butylamine to provide N-butyl-1-methyl-1H-imidazo[4,5-c]quinolin-4-amine, m.p. 98°–100° C.

Using the method of Example 49 and starting with the indicated carboxylic acids and trialkyl ortho esters, the compounds of Formula V shown in Table VII were prepared.

TABLE VII

| Ex. No. | Intermediate of Formula (Example No.) | Ortho Ester; Carboxylic Acid | Compound of Formula V (melting point in °C.) |
|---|---|---|---|
| 174 | 194 | triethyl orthoformate; formic acid | 1-(n-octyl)-1H—imidazo-[4,5-c]quinoline (57–59) |
| 175 | 195 | triethyl orthoacetate; acetic acid | 1-(n-hexyl)-2-methyl-1H—imidazo[4,5-c]quinoline (88–90) |
| 176 | 195 | triethyl orthoformate; formic acid | 1-(n-hexyl)-1H—imidazo-[4,5-c]quinoline (75–77) |
| 178 | 196 | triethyl orthoformate; formic acid | 1-[1,2-(dimethyl)propyl]-1H—imidazo[4,5-c]-quinoline (83–85) |
| 179 | 197 | triethyl orthoformate; formic acid | 7,8-dimethoxy-1-isobutyl-1H—imidazo[4,5-c]quinoline (163–165) |
| 180 | 27 | tri(3-methylbutyl) orthoformate; no acid | 2-isobutyl-1-methyl-1H—imidazo[4,5-c]quinoline (125–127) |
| 181 | 26 | tri(3-methylbutyl) orthoformate; no acid | 1,2-di(isobutyl)-1H—imidazo[4,5-c]quinoline (93–95) |
| 182 | 130 Part B | tri(3-methylbutyl) orthoformate; no acid | 2-isobutyl-1-[2-(phenyl)ethyl]-1H—imidazo[4,5-c]-quinoline (92–94) |
| 183 | 26 | tri(n-octyl) orthoformate; no acid | 2-[n-heptyl]-1-isobutyl-1H—imidazo[4,5-c]quinoline (58–61) |

Using the method of Examples 133 and 171 and starting with the indicated intermediates, the compounds of Formula I shown in Table VIII were prepared.

TABLE VIII

| Ex. No. | Intermediate of Formula VIII (Example No.) | Compound of Formula I (melting point in °C.) |
|---|---|---|
| 184 | 200 Step (3) | 1-(n-hexyl)-4-hydroxy-1H—imidazo-[4,5-c]quinoline (266–268) |
| 185 | 225 | 7,8-dimethoxy-4-hydroxy-1-isobutyl-1H—imidazo[4,5-c]quinoline |

TABLE VIII-continued

| Ex. No. | Intermediate of Formula VIII (Example No.) | Compound of Formula I (melting point in °C.) |
|---|---|---|
|  |  | 291.5) |

EXAMPLE 186

Using the method of Example 164, 3-amino-4-phenylaminoquinoline from Example 36 was converted to yellow solid 2-mercapto-1-phenyl-1H-imidazo[4,5-c]quinoline, m.p. >300° C. Analysis: Calculated for $C_{16}H_{11}N_3S$: %C, 69.3; %H, 4.0; %N, 15.2; Found: %C, 68.9; %H, 4.1; %N, 15.0.

EXAMPLE 187

Part A

Using the method of Example 1, 4-chloro-3-nitroquinoline was reacted with 2-hydroxypropylamine to provide 4-(2-hydroxypropylamino)-3-nitroquinoline.

Part B

Using the method of Example 26, 4-(2-hydroxypropylamino)-3-nitroquinoline was reduced to 3-amino-4-(2-hydroxypropylamino)quinoline.

Part C

A mixture of 32.9 g of 3-amino-4-(2-hydroxypropylamino)quinoline in 100 ml of triethyl orthoformate and 10 drops of formic acid was heated at 150° C. for two hours. The mixture was evaporated under vacuum, then 200 ml of water was added and the pH was adjusted to pH 2 to 3 with concentrated hydrochloric acid. The solution was basified with ammonium hydroxide, then with 50 percent sodium hydroxide solution. An oily product eventually solidified and was separated by filtration. Recrystallization from a mixture of hexane and dichloromethane gave an off-white solid 1-(2-hydroxypropyl)-1H-imidazo[4,5-c]quinoline, m.p. 171° C.

EXAMPLE 188

Part A

Using the method of Example 1, 4-chloro-3-nitroquinoline was reacted with 2-(4-methoxyphenyl)ethylamine to provide 4-[2-(4-methoxyphenyl)ethylamino]-3-nitroquinoline.

Part B

Using the method of Example 26, 20.4 g (0.063 mole) of 4-[2-(4-methoxyphenyl)ethylamino]-3-nitroquinoline was reduced by hydrogen in 300 ml of toluene with 5% platinum on charcoal. The solvent was then evaporated to provide a residue of 3-amino-4-[2-(4-methoxyphenyl)ethylamino]quinoline. To this residue was added 28 g (0.19 mole) of triethyl orthoformate and the mixture was heated at about 125° C. for two hours. To this mixture was added about 100 ml of aqueous hydrochloric acid and the mixture was heated on a steam bath for thirty minutes. After cooling, the precipitate was separated by filtration, washed sequentially with isopropanol and diethyl ether, and dried. To the solid was added water and ammonium hydroxide, after which the mixture was cooled and the solid was separated by filtration. A portion (3.5 g) of the solid was dissolved in isopropanol, and acidified with hydrochloric acid. The solid was separated by filtration, washed with isopropanol and dried to provide 1-[2-(4-methoxyphenyl)ethyl]-1H-imidazo[4,5-c]quinoline hydrochloride hydrate, m.p. 209°–213° C. Analysis: Calculated for $C_{19}H_{17}N_3O \cdot HCl \cdot \frac{1}{2}H_2O$: %C, 66.0; %H, 5.4; %N, 12.2; Found: %C, 66.1; %H, 5.3; %N, 12.3.

EXAMPLE 189

Part A

Using the method of Example 1, 4-chloro-3-nitroquinoline was reacted with 2-hydroxy-2-methylpropylamine to provide 4-(2-hydroxy-2-methylpropylamino)-3-nitroquinoline, m.p. 234°–244° C.(dec.). Analysis: Calculated for $C_{13}H_{15}N_3O_3$: %C, 59.8; %H, 5.8; %N, 16.0; Found: %C, 59.8; %H, 5.9; %N, 16.1.

Part B

Using the method of Example 26, 7.0 g (0.027 mole) of 4-(2-hydroxy-2-methylpropylamino)-3-nitroquinoline, 1 g of platinum on charcoal, 200 ml of toluene and 150 ml of ethanol was hydrogenated on a Paar apparatus. The solution was filtered, then evaporated to dryness to provide 3-amino-4-(2-hydroxy-2-methylpropylamino)quinoline was a solid residue. To the residue was added 50 ml of triethyl orthoformate and 5 drops of formic acid. The solution was heated at 135° to 140° C. for one hour, then allowed to stand for about 16 hours. The product was separated by filtration, dissolved in hydrochloric acid and reprecipitated with sodium hydroxide solution. The product was recrystallized from ethanol to provide 1-(2-hydroxy-2-methylpropyl)-1H-imidazo[4,5-c]quinoline, m.p. 169°–170° C. Analysis: Calculated for $C_{14}H_{15}N_3O \cdot H_2O$: %C, 64.8; %H, 6.6; %N, 16.2; Found: %C, 65.1; %H, 6.6; %N, 16.4.

Part C

A solution of 4.0 g (0.017 mole) of 1-(2-hydroxy-2-methylpropyl)-1H-imidazo[4,5-c]quinoline in 3.8 ml of acetic anhydride and 50 ml of pyridine was heated on a steam bath for one hour, diluted with 25 ml of methanol and heated again on the steam bath for fifteen minutes. The solution was evaporated to dryness, then co-evaporated with heptane. The solid residue was dried, then a mixture of 3.6 ml of 30 percent hydrogen peroxide and 50 ml of acetic acid was added. The mixture was heated at 60° C. for four hours, then one ml of hydrogen peroxide was added and the solution was maintained at 60° to 65° C. for 16 hours. Evaporation of the solution provided a solid residue. Infrared spectral analysis of the crude solid showed partial acetylation to the desired product, 1-(2-acetoxy-2-methylpropyl)-1H-imidazo[4,5-c]quinolin-5-oxide.

Part D

To a stirred solution of 1.5 g of crude 1-(2-acetoxy-2-methylpropyl)-1H-imidazo[4,5-c]quinolin-5-oxide from Part C in 10 ml of dichloromethane and 2 ml of N,N-dimethylformamide was added 0.843 g (0.0055 mole) of phosphorus oxychloride. After stirring for one hour, the mixture was evaporated to dryness. Hydrochloric acid was added to the residue, then the mixture was basified with ammonium hydroxide. The product was separated by filtration, washed with water and dried. Recrystallization from ethanol of a portion of the product provided 4-chloro-1-(2-hydroxy-2-methylpropyl)-1H-imidazo[4,5-c]quinoline, m.p. 196°–199° C. Analysis: Calculated for $C_{14}H_{14}ClN_3O$: %C, 61.0; %H, 5.2; %N, 15.2; Found: %C, 60.9; %H, 5.3; %N, 15.1.

Alternative Reaction Replacing Step (C) Above

A mixture of 2.4 g (0.01 mole) of 1-(2-hydroxy-2-methylpropyl)-1H-imidazo[4,5-c]quinoline, 2.5 ml of acetic acid and 1.7 g of 30% aqueous hydrogen peroxide (0.015 mole) were heated at 65°–70° C. for six and one-half hours. The solvent was evaporated under a stream of nitrogen. The resulting residue was co-evaporated with heptane in vacuo. The residue was then added to water and made basic by adding ammonium hydroxide. The solid was filtered, washed with water and dried to give 2.0 g of product by thin layer chromatography was found to contain 1 major component.

Using the method of Example 1 and starting with the 4-chloro-3-nitroquinolines shown, the following compounds of Formula III were prepared.

TABLE IX

| Ex. No. | Quinoline Starting Material of Formula II | Primary Amine Starting Material | Intermediate of Formula III |
| --- | --- | --- | --- |
| 190 | 4-chloro-3-nitroquinoline | n-octylamine | 3-nitro-4-(n-octylamino)quinoline |
| 191 | 4-chloro-3-nitroquinoline | n-hexylamine | 4-(n-hexylamino)-3-nitroquinoline |
| 192 | 4-chloro-3-nitroquinoline | 1,2-dimethylpropylamine | 1-[1,2-(dimethyl)propylamino]-3-nitroquinoline |
| 193 | 4-chloro-7,8-dimethoxy-3-nitroquinoline | isobutylamine | 7,8-dimethoxy-4-isobutylamino-3-nitroquinoline |

Using the method of Example 26 and starting with the indicated intermediates of Formula III, the intermediates of Formula IV shown in Table X were prepared.

TABLE X

| No. | Intermediate of Formula III (Example No.) | Intermediate of Formula IV |
| --- | --- | --- |
| 194 | 190 | 3-amino-4-(n-octylamino)quinoline |
| 195 | 191 | 3-amino-4-(n-hexylamino)quinoline |
| 196 | 192 | 3-amino-4-[1,2-(dimethyl)propylamino]quinoline |
| 197 | 193 | 3-amino-7,8-dimethoxy-4-isobutylaminoquinoline |

EXAMPLE 198

Part A

Using the method of Example 74, the compound of Example 176 was converted to 1-(n-hexyl)-1H-imidazo[4,5-c]quinolin-5-oxide.

Part B

Using the method of Example 96 the compound from Part A was converted to 4-chloro-1-(n-hexyl)-1H-imidazo[4,5-c]quinoline.

EXAMPLE 199

Part A

Using the method of Example 74 the compound of Example 179 was converted to 7,8-dimethoxy-1-isobutyl-1H-imidazo[4,5-c]quinolin-5-oxide.

Part B

Using the method of Example 96 the compound from Part A was converted to 4-chloro-7,8-dimethoxy-1-isobutyl-1H-imidazo[4,5-c]quinoline.

EXAMPLE 200

Step (1)

To a solution of 22.5 g (0.0823 mole) of 4-(n-hexyl)amino-3-nitroquinoline in 300 ml of toluene was added about 1.0 g of 5% platinum on charcoal and the mixture was hydrogenated on a Paar apparatus for 1.5 hours. Filtration followed by evaporation in vacuo provided a residue of 3-amino-4-(n-hexyl)aminoquinoline as an orange solid. Thin layer chromatographic analysis of the product on silica gel, eluting with methanol, showed one spot at $R_f=0.73$ and a trace at $R_f=0.35$.

Step (2)

The crude reaction product obtained by the method of Step (1) above from 22.5 g of 4-(n-hexyl)amino-3-nitroquinoline was mixed with 17.1 (0.1152 mole) of triethyl orthoformate and the mixture was heated at 130° C. for 2.5 hours. Evaporation provided a residue which was analyzed by thin layer chromatography on a silica gel plate, eluting with methanol. One spot was detected at $R_f=0.8$. A small sample of the residue was recrystallized once from diethyl ether to provide solid 1-(n-hexyl)-1H-imidazo[4,5-c]quinoline, m.p. 75°–77° C. Analysis: Calculated for $C_{16}H_{19}N_3$: %C, 75.85; %H, 7.55; %N, 16.6; Found: %C, 75.7; %H, 7.7; %N, 16.7

Step (3)

The crude reaction product from Step (2) above was diluted with 125 ml of glacial acetic acid and 14.0 g (0.1235 mole) of 30% hydrogen peroxide, and the mixture was heated at a bath temperature of 70° C. for 22 hours. The glacial acetic acid was removed by adding heptane and by then effecting an azeotropic distillation. The residue was diluted and neutralized with saturated sodium bicarbonate solution. The solid obtained was separated by filtration, washed with water, slurried in diethyl ether, separated by filtration and dried. Recrystallization from ethyl acetate provided 11.8 g of solid 1-(n-hexyl)-1H-imidazo[4,5-c]quinolin-5-oxide, m.p. 153°–158° C.

Step (4)

To a mixture of 6.1 ml (0.0657 mole) of phosphorus oxychloride and 80 ml of N,N-dimethylformamide was added gradually, with cooling to 10°–20° C., 11.8 g (0.0438 mole) of 1-(n-hexyl)-1H-imidazo[4,5-c]quinolin-5-oxide. The solution was allowed to stand at 20° C. for 15 minutes, and was then heated on a steam bath for 30 minutes. The solution was cooled and poured over ice with stirring. To the mixture was added concentrated ammonium hydroxide to adjust the pH to 8 to 9. The solid was separated by filtration, washed sequentially with water and diethyl ether, and dried. Recrystallization of a small portion of product from 1:1 ethyl acetate;hexane provided white solid 4-chloro-1-(n-hexyl)-1H-imidazo[4,5-c]quinoline, m.p. 106°–108° C. Analysis: Calculated for $C_{16}H_{18}ClN_3$; %C 66.8; %H, 6.3; %N, 14.6; Found %C, 66.8; %H, 6.1; %N, 14.4.

Using the method of Example 1 and/or 2, and starting with the indicated substituted quinolines and primary amines, the following compounds of Formula V were prepared (Table XI)

TABLE XI

| Ex. No. | Quinoline Starting Material of Formula IV | Primary Amine Starting Material | Intermediate of Formula V (m.p. in.°C.) |
|---|---|---|---|
| 201 | 4-chloro-3-nitroquinoline | 4-chlorobenzylamine | 4-(4-chlorobenzylamino)-3-nitroquinoline (175–177) |
| 202 | 4-chloro-3-nitroquinoline | n-otylamine | 4-(n-octylamino)-3-nitroquinoline (50–52) |
| 203 | 4-chloro-3-nitroquinoline | 1-(phenyl)ethylamine | 4-[1-(phenyl)ethylamino]-3-nitroquinoline (138–141) |
| 204 | 4-chloro-3-nitroquinoline | 1,3-dimethylbutylamine | 4-(1,3-dimethylbutylamino)-3-nitroquinoline (66–68) |
| 205 | 4-chloro-6,7-dimethoxy-3-nitroquinoline | isobutylamine | 6,7-dimethoxy-4-isobutylamino-3-nitroquinoline |

EXAMPLE 206

Using the method of Example 200, Step (1), 6,7-dimethoxy-4-isobutylamino-3-nitroquinoline was reduced to 3-amino-6,7-dimethoxy-4-isobutylaminoquinoline, m.p. 159°–161° C.

Using the method of Example 200 Step (1), various intermediates of Formula V were reduced to provide 3-aminoquinolines of Formula VI. These intermediates of Formula VI (usually crude) were cyclized using the method of Example 200, Step (2), to provide the intermediates of Formula VII shown in Table XII.

TABLE XII

| Ex. No. | Intermediate of Formula V (Example) | Intermediate of Formula VI | Ortho Ester | Intermediate of Formula VII (m.p. in °C.) |
|---|---|---|---|---|
| 207 | 48 | 3-amino-4-(4-chlorobenzyl-amino)quinoline | triethyl orthoacetate | 1-(4-chlorobenzyl)-2-methyl-1H—imidazo[4,5-c]quinoline (178–180) |
| 208 | 200, Step (2) | 3-amino-4-(n-hexylamino)-quinoline | triethyl orthoacetate | 1-(n-hexyl)-2-methyl-1H—imidazo-[4,5-c]quinoline (88–90) |
| 209 | 2 | 3-amino-4-(n-methylamino)-quinoline | triethyl orthoisobutyrate | 2-isobutyl-1-methyl-1H—imidazo[4,5-c]-quinoline (125–127) |
| 210 | 202 | 3-amino-4-(n-octylamino)quinoline | triethyl orthoformate | 1-(n-octyl)-1H—imidazo[4,5-c]quinoline (not taken) |
| 211 | 1 | 3-amino-4-(isobutylamino)quinoline | triethyl orthoisobutyrate | 1,2-diisobutyl-1H—imidazo[4,5-c]-quinoline (93–95) |
| 212 | 130, Part B | 3-amino-4-[2-(phenyl)ethyl-amino]quinoline | triethyl ortholsobutyrate | 2-isobutyl-1-[2-(phenyl)ethyl]-1H—imidazo[4,5-c]quinoline (92–94) |
| 213 | 203 | 3-amino-4-[1-(phenyl)ethyl- | triethyl orthoformate | 1-[1-(phenyl)ethyl]-1H—imidazo[4,5-c] |

TABLE XII-continued

| Ex. No. | Intermediate of Formula V (Example) | Intermediate of Formula VI | Ortho Ester | Intermediate of Formula VII (m.p. in °C.) |
|---|---|---|---|---|
| | | amino]quinoline | | quinoline(172–174) |
| 214 | 204 | 3-amino-4-(1,3-dimethyl-butylamino)quinoline | triethyl orthoformate | 1-(1,3-dimethylbutyl)-1H—imidazo-[4,5-c]quinoline (83–85) |
| 215 | 206 | 3-amino-6,7-dimethoxy-4-(isobutylamino)quinoline | triethyl orthoformate (a few drops of formic acid) | 7,8-dimethoxy-1-isobutyl-1H—imidazo-[4,5-c]quinoline (163–165) |

Using the method of Example 200, step (3), intermediate compounds of Formula VIII shown in Table XIII were prepared.

TABLE XIII

| Ex. No. | Intermediate of Formula VII (Example No.) | Intermediate of Formula VIII (m.p. in °C.) |
|---|---|---|
| 216 | 207 | 1-(4-chlorobenzyl)-2-methyl-1H-imidazo[4,5-c]quinolin-5-oxide (251–253) |
| 217 | 67 | 1-(n-butyl)-1H—imidazo[4,5-c]quinolin-5-oxide (161–163) |
| 218 | 208 | 1-(n-hexyl)-2-methyl-1H—imidazo[4,5-c]quinolin-5-oxide (138–148 crude) |
| 219 | 209 | 2-isobutyl-1-methyl-1H—imidazo[4,5-c]quinolin-5-oxide (202–204) |
| 220 | 210 | 1-(n-octyl)-1H—imidazo[4,5-c]quinolin-5-oxide (86–90) |
| 221 | 211 | 1,2-diisobutyl-1H—imidazo[4,5-c]quinolin-5-oxide (153–156) |
| 222 | 212 | 2-isobutyl-1-[2-(phenyl)ethyl]-1H—imidazo[4,5-c]quinolin-5-oxide (158–160) |
| 223 | 213 | 1-[1-(phenyl)ethyl]-1H—imidazo[4,5-c]quinolin-5-oxide (not taken), yellow solid, satisfactory elemental analysis |
| 224 | 214 | 1-(1,3-dimethylbutyl)-1H—imidazo[4,5-c]quinolin-5-oxide (not taken), light orange solid |
| 225 | 215 | 7,8-dimethoxy-1-isobutyl-1H—imidazo[4,5-c]quinolin-5-oxide (not taken) |

Using the method of Example 200, Step (4), intermediate compounds of Formula IX shown in Table XIV were prepared.

TABLE XIV

| Ex. No. | Intermediate of Formula VIII (Example No.) | Intermediate of Formula IX (m.p. in °C.) |
|---|---|---|
| 226 | 90 | 4-chloro-2-methyl-1-[2-(phenyl)ethyl]-1H—imidazo[4,5-c]quinoline (138–140) |
| 227 | 216 | 1-(4-chlorobenzyl)-4-chloro-2-methyl-1H—imidazo[4,5-c]quinoline (240–242) |
| 228 | 217 | 1-(n-butyl)-4-chloro-1H—imidazo[4,5-c]quinoline (122–124) |
| 229 | 218 | 4-chloro-1-(n-hexyl)-2-methyl-1H—imidazo[4,5-c]quinoline (119–121) |
| 230 | 219 | 4-chloro-2-isobutyl-1-methyl-1H—imidazo[4,5-c]quinoline (158–160) |
| 231 | 220 | 4-chloro-1-(n-octyl)-1H—imidazo[4,5-c]quinoline (86–90) |
| 232 | 221 | 4-chloro-1,2-diisobutyl-1H—imidazo[4,5-c]quinoline (137–139) |
| 233 | 222 | 4-chloro-2-isobutyl-1-[2-(phenyl)ethyl]-1H—imidazo[4,5-c]quinoline (151–153) |
| 234 | 223 | 4-chloro-1-[1-(phenyl)ethyl]-1H—imidazo[4,5-c]quinoline (not taken), white solid, satisfactory elemental analysis |
| 235 | 224 | 4-chloro-1-(1,3-dimethylbutyl)-1H—imidazo[4,5-c]quinoline (111–114) |
| 236 | 225 | 4-chloro-7,8-dimethoxy-1-isobutyl-1H—imidazo[4,5-c]quinoline (185–188) |

EXAMPLE 237

To 70 ml of acetic anhydride was added 13.0 g (0.0539 mole) of 1-isobutyl-1H-imidazo[4,5-c]quinolin-5-oxide. The solution was heated on a steam bath for 10 minutes, then allowed to cool. The precipitate was separated by filtration, washed with ethanol, and dried. Recrystallization from N,N-dimethylformamide provided 1-isobutyl-1H-imidazo[4,5-c]quinoline-4-ol, m.p. >300° C. Analysis: Calculated for $C_{14}H_{15}N_3O$: %C, 69.7; %H, 6.3; %N, 17.4; Found: %C, 69.8; %H, 6.4; %N, 17.6.

EXAMPLE 238

Step (A)

To 50.0 g (0.269 mole) of 4-hydroxy-3-nitroquinoline in 300 ml of N,N-dimethylformamide in a 500 ml erlenmeyer flask was added, gradually, 44.3 g (0.2892 mole) of phosphorus oxychloride. The resulting mixture was heated on a steam bath for about 15 minutes, and was then poured onto ice with stirring. After neutralization with saturated sodium bicarbonate solution, the resulting light-colored solid was separated by filtration and washed sequentially with a saturated sodium bicarbonate solution and water. The solid was dissolved in methylene chloride and the solution obtained was dried over sodium chloride, filtered and transferred to a 2 l erlenmeyer flask. Triethylamine (159.6 g, 1.577 moles) was added at one time, followed by the slow addition of 21.2 g (0.2892 mole) of isobutylamine. After the isobutylamine had been added, the mixture was heated on a steam bath for about 30 minutes. The methylene chloride was removed by rotary evaporation. Water was added to the residue obtained, and concentrated hydrochloric acid was subsequently added to dissolve the residue. The solution was filtered, and the filtrate was brought to pH 8–9 with concentrated ammonium hydroxide. The resulting yellow solid was filtered, washed with water, and dried to provide 73.4 g of crude 4-isobutylamino-3-nitroquinoline, m.p. 114°–118° C. The product was further purified by recrystallization from ethanol.

Step (B)

4-isobutylamino-3-nitroquinoline (31.5 g, 0.1284 moles) from Step (A) above, was dissolved in 300 ml of toluene, and 1 g of 5% platinum on carbon was added thereto. The resulting mixture was hydrogenated on a Parr apparatus for one and one-half hours. The mixture was then heated and filtered. Toluene was removed from the filtrate by rotary evaporation to provide 27.8 g of crude 3-amino-4-(isobutylamino)quinoline. Recrystallization twice from ethyl acetate/hexane provided 18.8 g of purified product, m.p. 98°–100° C. Analysis: Calculated for $C_{13}H_{17}N_3$: %C, 72.5; %H, 8.0; %N, 19.5; Found: %C, 73.2; %H, 7.8; %N, 19.7.

Step (C)

To 10.0 g (0.0464 mole) of 3-amino-4-(isobutylamino)quinoline (from Step (B) above) was added 9.0 g (0.0604 mole) of triethyl orthoformate, and the mixture was heated at 125°–130° C. for three hours. The mixture was then allowed to cool to room temperature, and 30 ml of glacial acetic acid and 7.9 g (0.0696 mole) of 30% hydrogen peroxide solution were added thereto. The resulting mixture was heated at 68°–70° C. in an oil bath for about 24 hours. The glacial acetic acid was removed by azeotropic distillation using heptane as the co-solvent. Saturated sodium bicarbonate solution was added to the residue to bring it to neutrality. The beige solid which precipitated was filtered, washed with water, and dried to provide 10.0 g of crude product 1-isobutyl-1H-imidazo[4,5-c]quinolin-5-oxide. This solid was slurried in a small amount of cold acetone, and was then separated by filtration, washed and dried to provide 6.2 g of purified product having a m.p. of 205°–209° C.

Step (D)

To 40 ml of cold N,N-dimethylformamide (10°–20° C.) was added slowly 5.9 g (0.0385 mole) of phosphorus oxychloride with swirling, the temperature of the mixture being maintained at 10°–20° C. 1-Isobutyl-1H-imidazo[4,5-c]quinolin-5-oxide (6.2 g; 0.0257 mole) from Step (C) above was added gradually with swirling and cooling. After addition was complete, the solution was allowed to stand at room temperature for about 30 minutes with occasional swirling. The solution was then heated on a steam bath for thirty minutes. After allowing it to cool, the solution was poured onto ice with stirring, and the resulting mixture was brought to pH 8–9 with concentrated ammonium hydroxide. The resulting off-white solid was filtered, washed with water, rinsed with ether, and dried to provide 6.0 g of crude 4-chloro-1-isobutyl-1H-imidazo[4,5-c]quinoline having a m.p. of 135°–138° C.

What is claimed is:

1. A compound of the formula

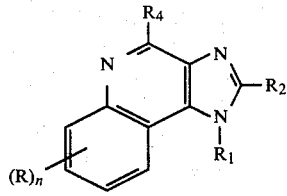

wherein $R_1$ is selected from the group consisting of hydrogen, alkyl of one to about ten carbon atoms, hydroxyalkyl of one to about six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkyl alkanoate wherein the alkyl moiety contains one to about four carbon atoms and the alkanoate moiety contains two to about four carbon atoms, alkoxy of one to about four carbon atoms and halogen, with the proviso that if said benzene ring is substituted by two of said moieties, then said moieties together contain no more than 6 carbon atoms; $R_2$ is selected from the group consisting of hydrogen, trifluoromethyl, hydroxyalkyl of one to about six carbon atoms, aminoalkyl of one to about four carbon atoms, alkanamidoalkyl wherein each alkyl radical is one to about four carbon atoms, benzylthio, mercapto, alkylthio of one to about four carbon atoms, and alkyl of one to about eight carbon atoms, with the proviso that when $R_2$ is mercapto and $R_1$ is alkyl, $R_1$ is alkyl of one to four carbon atoms; $R_4$ is selected from the group consisting of hydrogen, chloro, alkoxy of one to about four carbon atoms, hydroxy, alkylamino of one to about four carbon atoms, dialkylamino wherein each alkyl radical contains one to about four carbon atoms, alkyl of one to about four carbon atoms, phenylthio, alkylthio of one to about four carbon atoms, and morpholino, with the proviso that when $R_2$ is mercapto, alkylthio or benzylthio, $R_4$ is hydrogen or alkyl; and each R is independently selected from the group consisting of alkoxy of one to four carbon atoms, alkyl of one to four carbon atoms, and halogen, and n is an integer from 0 to 2, with the proviso that if n is 2, then said R substituents together contain no more than 6 carbon atoms; or a pharmaceutically acceptable acid addition salt thereof.

2. A compound according to claim 1 wherein $R_4$ is hydrogen.

3. A compound according to claim 2 wherein R is hydrogen.

4. A compound according to claim 1 selected from the group consisting of:
1,8-dimethyl-2-hydroxymethyl-1H-imidazo[4,5-c]quinoline,
1,8-dimethyl-2-trifluoromethyl-1H-imidazo[4,5-c]quinoline,
1-methyl-4-methoxy-1H-imidazo[4,5-c]quinoline,
1-isobutyl-8-methyl-1H-imidazo[4,5-c]quinoline,
1-ethyl-2-methyl-1H-imidazo[4,5-c]quinoline,
1-ethyl-1H-imidazo[4,5-c]quinoline,
1-phenyl-1H-imidazo[4,5-c]quinoline,
1-(4-fluorophenyl)-1H-imidazo[4,5-c]quinoline,
1-isobutyl-1H-imidazo[4,5-c]quinolin-4-ol,
7,8-dimethoxy-1-isobutyl-1H-imidazo-[4,5-c]quinoline,
7,8-dimethoxy-1-isobutyl-1H-imidazo[4,5-c]quinolin-4-ol,
and 4-chloro-1-methyl-1H-imidazo[4,5-c]quinolin-4-ol.

5. The compound 1-isobutyl-1H-imidazo[4,5-c]quinolin-4-ol according to claim 1.

6. A compound of the formula

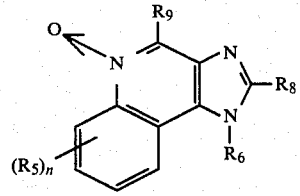

wherein $R_6$ is selected from the group consisting of alkyl of one to about ten carbon atoms, hydroxyalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkyl alkanoate wherein the alkyl moiety contains one to about four carbon atoms and the alkanoate moiety contains two to about four carbon atoms, alkoxy of one to about four carbon atoms and halogen, with the proviso that if said benzene ring is substituted by two of said moieties, then said moieties together contain no more than 6 carbon atoms; $R_8$ is selected from the group consisting of hydrogen, trifluoromethyl, hydroxyalkyl of one to about six carbon atoms, aminoalkyl of one to about four carbon atoms, alkyl of one to about eight carbon atoms and alkanamidoalkyl wherein each alkyl radical is one to about four carbon atoms; $R_9$ is hydrogen or methyl; and each $R_5$ is independently selected from the group consisting of halogen, alkoxy of one to about four carbon atoms and alkyl of one to about four carbon atoms, and n is an integer from 0 to 2, with the proviso that if n is 2, then said $R_5$ substituents together contain no more than 6 carbon atoms.

7. A compound of the formula

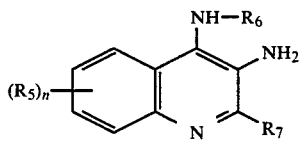

wherein each $R_5$ is independently selected from the group consisting of alkyl of one to about four carbon atoms, alkoxy of one to about four carbon atoms and halogen, and n is an integer from 0 to 2, with the proviso that if n is 2, then said $R_5$ substituents together contain no more than 6 carbon atoms; $R_6$ is selected from the group consisting of hydroxyalkyl of one to about six carbon atoms and cyclohexylmethyl; and $R_7$ is selected from the group consisting of alkyl of one to about four carbon atoms and hydrogen.

8. A compound of the formula

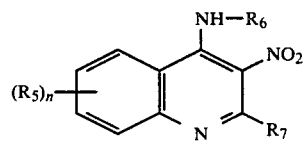

wherein each $R_5$ is independently selected from the group consisting of alkyl of one to about four carbon atoms, alkoxy of one to about four carbon atoms and halogen, and n is an integer from 0 to 2, with the proviso that if n is 2, then said $R_5$ substituents together contain no more than 6 carbon atoms; $R_6$ is selected from the group consisting of hydroxyalkyl of one to about six carbon atoms and cyclohexylmethyl; and $R_7$ is selected from the group consisting of alkyl of one to about four carbon atoms and hydrogen.

9. A bronchodilator pharmaceutical composition comprising a compound of claim 1 and a pharmaceutically acceptable vehicle, said compound being present in an amount effective to cause bronchodilation.

10. A method for obtaining bronchodilation in a mammal comprising administering to said mammal a compound according to claim 1 in an amount sufficient to cause bronchodilation.

* * * * *